US006521438B1

(12) United States Patent
Davis et al.

(10) Patent No.: US 6,521,438 B1
(45) Date of Patent: Feb. 18, 2003

(54) CHEMORECEPTORS IN PLANT PARASITIC NEMATODES

(75) Inventors: Eric L. Davis, Raleigh, NC (US); Yitang Yan, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/435,376

(22) Filed: Nov. 5, 1999

(51) Int. Cl.[7] ............................ C12N 1/00; C12N 1/14; C12N 15/00; C12N 5/00; C07H 21/04

(52) U.S. Cl. ................. 435/243; 435/254.2; 435/320.1; 435/325; 435/348; 435/410; 536/23.1; 536/24.3

(58) Field of Search ........................... 435/6, 91.1, 243, 435/320.1, 254.2, 325, 348, 410; 536/23.1, 24.3

(56) References Cited

PUBLICATIONS

Russell et al., J. Mol. Bol. 1994, vol. 244, pp 332–350.*
Blaxter et al.; Letters to Nature, *Nature*, 392 (Mar. 15, 1998). Fig. 2 Only.
Yu et al.; Guanylyl Cyclase Expression in Specific Sensory Neuros: A New Family of Chemosenory Receptors, *Proc. Natl. Acad. Sci. USA*, 94:3384–3387 (1997).

* cited by examiner

*Primary Examiner*—W. Gary Jones
*Assistant Examiner*—Jehanne Souaya
(74) *Attorney, Agent, or Firm*—Myers Bigel Sibley & Sajovec

(57) ABSTRACT

Isolated DNA encoding a nematode guanylyl cyclase chemoreceptor is disclosed. Preferably, the encoded nematode guanylyl cyclase chemoreceptor is selected from the group consisting of order Tylenchida and order Aphelenchida chemoreceptors. Also disclosed are vectors and cells containing the DNA, the encoded proteins, oligonucleotides that bind thereto, and methods of using the same.

12 Claims, 1 Drawing Sheet

CHEMORECEPTORS IN PLANT PARASITIC NEMATODES

FIELD OF THE INVENTION

The present invention concerns isolated DNA encoding chemoreceptors of plant parasitic nematodes, cells that express such DNA, the proteins so expressed, and methods of use thereof.

BACKGROUND OF THE INVENTION

Annual crop losses to plant-parasitic nematodes (soil-dwelling microscopic worms) are estimated to exceed 70 billion dollars world-wide. The soybean cyst nematode (SCN), *Heterodera glycines*, causes about one billion in annual soybean losses in the United States alone. Environmental restrictions in the use of toxic nematicides and limitations in available plant resistance schemes to nematodes have prompted an urgent need for alternative management strategies to reduce nematode-related damage in agriculture.

One way to control nematodes is by understanding and specifically interfering with the nematode's ability to locate and feed from plant roots. Like most plant-parasitic nematodes, infective juveniles of SCN migrate in the soil and use their neurosensory organs to follow chemical signals emanating from host roots that they will attack Chemoreceptor molecules have been identified in the model nematode, *Caenorhabditis elegans*, as described in S. Yu et al., *Proc. Natl. Acad. Sci. USA* 94, 3384–3387 (1997). However, essentially nothing is known about putative chemoreceptors in plant-parasitic nematodes. Accordingly, there is a continued need for more information about the chemoreceptors of plant-parasitic nematodes.

SUMMARY OF THE INVENTION

A first aspect of the present invention is an isolated DNA encoding a nematode guanylyl cyclase chemoreceptor selected from the group consisting of: (a) isolated DNA having a nucleotide sequence selected from the group consisting of SEQ ID NO: 1, SEQ ID NO: 3, SEQ ID NO: 4, and SEQ ID NO: 6; (b) isolated DNA that hybridizes to DNA of (a) above under stringent conditions and encodes a nematode guanylyl cyclase chemoreceptor; and (c) isolated DNA that differs from the DNA of (a) or (b) above due to the degeneracy of the genetic code, and encodes a nematode guanylyl cyclase chemoreceptor encoded by (a) or (b) above.

In one particular embodiment of the invention, the isolated DNA is selected from the group consisting of: (a) isolated DNA having a nucleotide sequence selected from the group consisting of SEQ ID NO: 4 and SEQ ID NO: 6; (b) isolated DNA that hybridizes to DNA of (a) above under stringent conditions in which said isolated DNA does not hybridize to DNA having a nucleotide sequence of SEQ ID NO: 1, and encodes a nematode guanylyl cyclase chemoreceptor; and (c) isolated DNA that differs from the DNA of (a) or (b) above due to the degeneracy of the genetic code, and encodes a nematode guanylyl cyclase chemoreceptor encoded by (a) or (b) above.

In another particular embodiment of the invention, the isolated DNA is selected from the group consisting of: (a) isolated DNA having a nucleotide sequence selected from the group consisting of SEQ ID NO: 1 and SEQ ID NO: 3; (b) isolated DNA that hybridizes to DNA of (a) above under stringent conditions and encodes a nematode guanylyl cyclase chemoreceptor; and (c) isolated DNA that differs from the DNA of (a) or (b) above due to the degeneracy of the genetic code, and encodes a nematode guanylyl cyclase chemoreceptor encoded by (a) or (b) above.

In another particular embodiment of the invention, the isolated DNA is selected from the group consisting of: (a) isolated DNA having a nucleotide sequence selected from the group consisting of SEQ ID NO: 4; (b) isolated DNA that hybridizes to DNA of (a) above under stringent conditions and encodes a nematode guanylyl cyclase chemoreceptor; and (c) isolated DNA that differs from the DNA of (a) or (b) above due to the degeneracy of the genetic code, and encodes a nematode guanylyl cyclase chemoreceptor encoded by (a) or (b) above.

In still another particular embodiment of the invention, the isolated DNA is selected from the group consisting of: (a) isolated DNA having a nucleotide sequence selected from the group consisting of SEQ ID NO: 6; (b) isolated DNA that hybridizes to DNA of (a) above under stringent conditions and encodes a nematode guanylyl cyclase chemoreceptor; and (c) isolated DNA that differs from the DNA of (a) or (b) above due to the degeneracy of the genetic code, and encodes a nematode guanylyl cyclase chemoreceptor encoded by (a) or (b) above.

Preferably, the encoded nematode guanylyl cyclase chemoreceptor is selected from the group consisting of order Tylenchida and order Aphelenchida chemoreceptors.

A second aspect of the invention is an oligonucleotide that specifically binds to isolated DNA as described above is a further aspect of the invention. Such an oligonucleotide may comprise DNA or RNA, or may be a synthetic oligonucleotide.

A third aspect of the invention is an antisense oligonucleotide that specifically binds to an mRNA transcript of a DNA as described above, along with DNAs that encode such antisense oligonucleotides.

A fourth aspect of the invention double-stranded RNA that is complementary to a DNA as described above and interferes with the expression thereof in a cell that expresses the encoded protein.

A fifth aspect of the invention is an expression cassette comprising a DNA as described above and a heterologous promoter operatively associated therewith, along with cells that contain such expression cassettes and express the encoded nematode guanylyl cyclase chemoreceptor (e.g., yeast cells, plant cells, insect cells).

A sixth aspect of the invention is an isolated nematode guanylyl cyclase chemoreceptor protein encoded by a DNA as described above (a protein of the invention), along with proteins or peptides (e.g., antibodies) that specifically bind to such nematode guanylyl cyclase chemoreceptor proteins.

A seventh aspect of the present invention is a method of screening a compound for the ability to disrupt plant parasitic nematode feeding or chemotaxis, said method comprising: determining whether or not said compound selectively binds to a nematode guanylyl cyclase chemoreceptor protein encoded by a DNA as described above. The presence of such binding indicating said compound is useful in disrupting plant parasitic nematode feeding or chemotaxis.

The foregoing and other objects and aspects of the present invention are explained in detail in the specification set forth below.

DETAILED DESCRIPTION OF THE PREFERRED EMBODIMENTS

Figure 1:
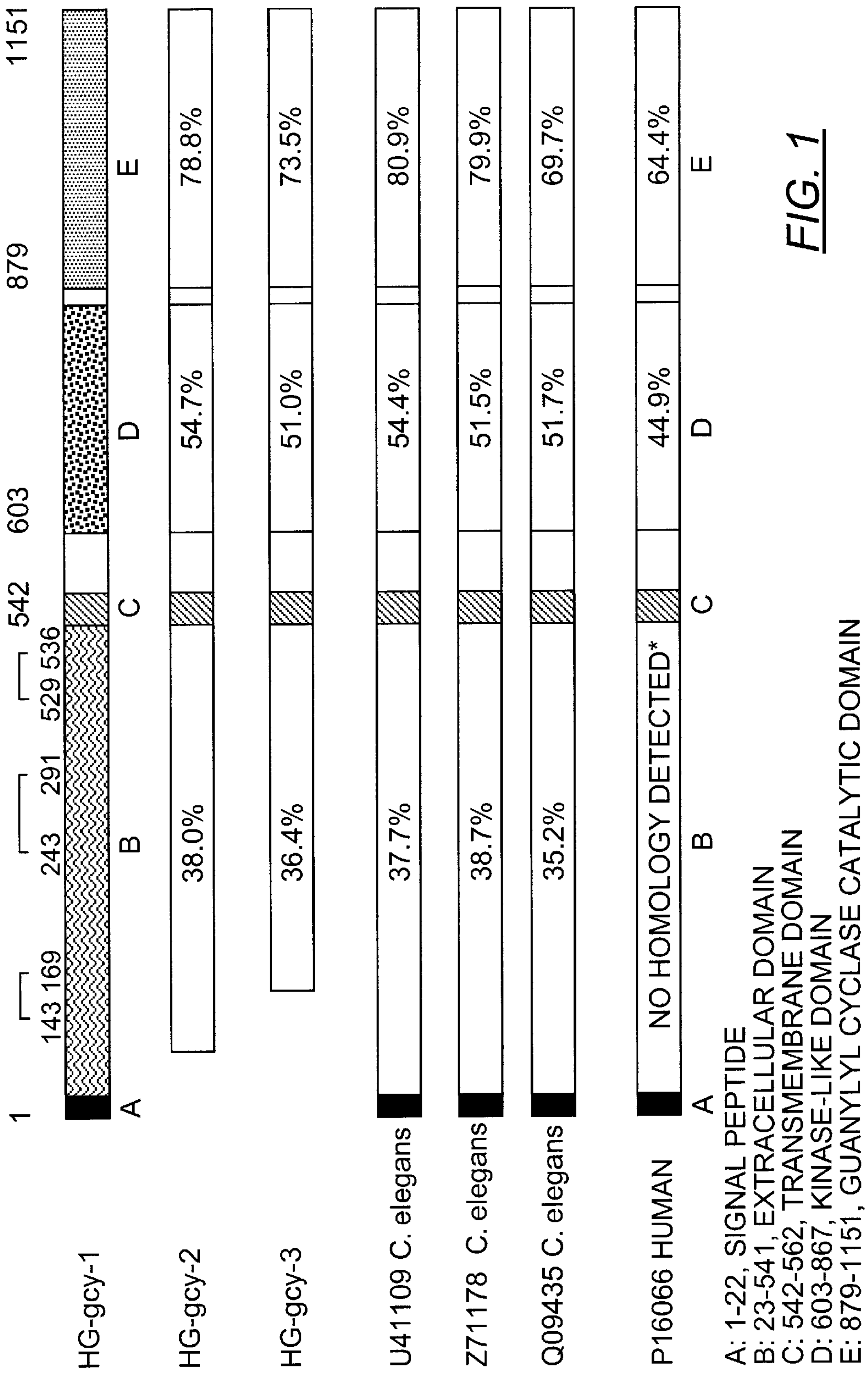
FIG. 1 provides a comparison of the guanylyl cyclase (gcy) domains of HG-gcy-1, HG-gcy-2, and HG-gcy-3 to various other guanylyl cyclases and proteins.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage.

The present invention may be carried out with plant parasitic, or plant feeding, nematodes. That is, chemoreceptors proteins of the present invention may be those of such nematodes, and isolated DNA may be isolated, directly or indirectly, from such nematodes. Examples of plant parasitic nematodes include, but are not limited to, cyst nematodes (Heteroderidae spp.), root knot nematodes (Meloidogyne spp.), lesion nematodes (Pratylenchus spp.), and reniform nematodes (Rotylenchulus spp.). In general, nematodes of the orders Tylenchida and Aphelenchida are preferred, particularly nematodes of the order Tylenchida. Nematodes of the Heteroderoidea superfamily are particularly preferred, the Heterodae family more preferred, and the genus Heterodera most preferred.

The production of cloned genes, recombinant DNA, vectors, transformed host cells, proteins and protein fragments by genetic engineering is discussed in greater detail below. It will be appreciated, however, that the techniques employed in carrying out the instant invention are well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

1. Isolated Nucleic Acids

Isolated DNA of the present invention can be of any species of origin, but is preferably isolated either directly or indirectly from plant parasitic nematodes as described above. Thus, polynucleotides that hybridize to DNA disclosed herein as SEQ ID NO:1, SEQ ID NO: 3, SEQ ID NO: 4, and/or SEQ ID NO: 6 (or fragments or derivatives thereof which serve as hybridization probes as discussed below) and which code on expression for a protein of the present invention (e.g., a protein according to SEQ ID NO:2), are also an aspect of the present invention.

Conditions which will permit other polynucleotides that code on expression for a protein of the present invention to hybridize to the aforesaid DNA can be determined in accordance with known techniques. For example, hybridization of such sequences may be carried out under conditions of reduced stringency, medium stringency or even stringent conditions (e.g., conditions represented by a wash stringency of 35–40% Formamide with 5×Denhardt's solution, 0.5% SDS and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively) to the aforesaid DNA in a standard hybridization assay. See, e.g, J. Sambrook et al., *Molecular Cloning, A Laboratory Manual* (2d Ed. 1989) (Cold Spring Harbor Laboratory). In general, sequences which code for proteins of the present invention and which hybridize to the DNAs disclosed herein will be at least 60% homologous, 70% homologous, 80% homologous and even 90% homologous or more with SEQ ID NO:1, SEQ ID NO:3, SEQ ID NO: 4, or SEQ ID NO: 6, respectively.

As noted above, in one particular embodiment of the invention, the isolated DNA is selected from the group consisting of: (a) isolated DNA having a nucleotide sequence selected from the group consisting of SEQ ID NO: 4 and SEQ ID NO: 6; (b) isolated DNA that hybridizes to DNA of (a) above under stringent conditions in which said isolated DNA does not hybridize to DNA having a nucleotide sequence of SEQ ID NO: 1, and encodes a nematode guanylyl cyclase chemoreceptor; and (c) isolated DNA that differs from the DNA of (a) or (b) above due to the degeneracy of the genetic code, and encodes a nematode guanylyl cyclase chemoreceptor encoded by (a) or (b) above. In this embodiment, the stringency of the wash conditions is routinely determined by adjusting wash stringency upward until the stringency meets the test of excluding hybridization to a nucleotide sequence of SEQ ID NO: 1.

Further, polynucleotides that code for proteins of the present invention, or polynucleotides that hybridize to nucleotides having a sequence as given in SEQ ID NO:1, SEQ ID NO:3, SEQ ID NO: 4, and/or SEQ ID NO: 6, as described above, but which differ in codon sequence from the given coding sequence due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

The invention also encompasses production of DNA sequences, or fragments thereof, which encode proteins of the invention, entirely by synthetic chemistry. Where modeled after the natural protein or DNA, such sequences may be considered to have been indirectly isolated from the species carrying the naturally occurring nucleotide or protein. After production, the synthetic sequence may be inserted into any of the many available expression vectors and cell systems using reagents that are well known in the art.

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties.

2. Oligonucleotides

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray.

As used herein, oligonucleotide includes "amplifiers", "primers", "oligomers", and "probes", as commonly defined in the art.

Knowledge of the nucleotide sequences disclosed herein can be used to generate hybridization probes which specifically bind to the DNA of the present invention or to mRNA produced by the transcription of such nucleotides to determine the presence of, amplify, or determine the overexpression of the proteins of the present invention. The oligonucleotides may also be used as active agents for the control of plant feeding nematodes as described above.

A label or detectable group may be conjugated to the oligonucleotide, if desired. A wide variety of labels and conjugation techniques are known by those skilled in the art and may be used in various nucleic acid and amino acid assays. Means for producing labeled hybridization or PCR probes for detecting sequences related to proteins of the invention oligolabeling, nick translation, end-labeling or PCR amplification using a labeled nucleotide. Alternatively, the sequences encoding proteins of the invention, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Assays for detecting the nucleotides of the invention, or the extent of amplification thereof, typically involve, first, contacting the cells or extracts of the cells containing nucleic acids therefrom with an oligonucleotide that specifically binds to proteins of the invention under conditions that permit access of the oligonucleotide to intracellular material, and then detecting the presence or absence of binding of the oligonucleotide thereto. Any suitable assay format may be employed (see, e.g., U.S. Pat. No. 4,358,535 to Falkow et al.; U.S. Pat. No. 4,302,204 to Wahl et al.; 4,994,373 to Stavrianopoulos et al; 4,486,539 to Ranki et al.; 4,563,419 to Ranki et al.; and 4,868,104 to Kurn et al.) (the disclosures of which applicant specifically intends be incorporated herein by reference).

3. Expression Vectors and Transgenic Cell Lines

A vector is a replicable DNA construct. Vectors are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformned host cells are cells which have been transformed or transfected with vectors containing DNA coding for proteins of the present invention need not express protein.

Suitable host cells include prokaryotes, yeast cells, or higher eukaryotic organism cells. Prokaryote host cells include gram negative or gram positive organisms, for example *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. See Bolivar et al., *Gene* 2, 95 (1977). Promoters most commonly used in recombinant microbial expression vectors include the betalactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res*. 8, 4057 (1980) and EPO App. Publ. No. 36,776) and the tac promoter (H. De Boer et al., *Proc. Natl. Acad. Sci. USA* 80, 21 (1983). The promoter and Shine-Dalgamo sequence (for prokaryotic host expression) are operably linked to the DNA of the present invention, i.e., they are positioned so as to promote transcription of the messenger RNA from the DNA.

Expression vectors should contain a promoter which is recognized by the host organism. This generally means a promoter obtained from the intended host. Promoters most commonly used in recombinant microbial expression vectors include the betalactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res*. 8, 4057 (1980) and EPO App. Publ. No. 36,776) and the tac promoter (H. De Boer et al., *Proc. Natl. Acad. Sci. USA* 80, 21 (1983). While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980). The promoter and Shine-Dalgarno sequence (for prokaryotic host expression) are operably linked to the DNA encoding the desired protein,. i.e., they are positioned so as to promote transcription of the protein messenger RNA from the DNA.

Eukaryotic microbes such as yeast cultures may be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or anautonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977). The presence of the trp1 lesion in the yeast host cell genome then provides an effective environment for detecting transformation by growth in the absence of tryptophan.

Suitable promoting sequences in yeast vectors include the promoters for metallothionein, 3-phospho-glycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and W1138, BHK, COS-7, CV, and MDCK cell lines. Expression vectors for such cells ordinarily include (if necessary) an origin of.replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculorivus expression vector (e.g., vectors derived from *Autographa californica* MNPV, Trichoplusia ni MNPV, *Rachiplusia ou* MNPV, or *Galleria ou* MNPV) may be employed to make proteins useful in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

In mammalian host cells, a number of viral-based expression systems may be utilized. In cases where an adenovirus is used as an expression vector, sequences encoding proteins of the invention may be ligated into an adenovirus transcription/translation complex consisting of the late promoter and tripartite leader sequence. Insertion in a non-essential E1 or E3 region of the viral genome may be used to obtain a viable virus which is capable of expressing proteins of the invention in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Rather than using vectors which contain viral origins of replication, one can transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival or transformants in culture medium that is toxic, or from which the cells cannot obtain critical nutrition without having taken up the marker protein.

4. Antibodies and Other Binding Proteins and Peptides

As used herein, the term "antibody" refers to intact molecules as well as fragments thereof, such as Fa, $F(ab')_2$, and Fc, which are capable of binding the epitopic determinant. Antibodies that bind proteins of the invention can be prepared using intact proteins or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit) from which antibodies or spleen cells are collected.

Antibodies that specifically bind to the proteins of the present invention (i.e., antibodies which bind to a single antigenic site or epitope on the proteins) are useful for a variety of diagnostic purposes.

Antibodies to proteins of the invention may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with a protein of the invention or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and Corynebacterium parvum are especially preferable.

Monoclonal antibodies to proteins of the invention may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) *Nature* 256:495–497; Kozbor, D. et al. (1985) *J. Immunol. Methods* 81:31–42; Cote, R. J. et al. (1983) *Proc. Natl. Acad. Sci.* 80:2026–2030; Cole, S. P. et al. (1984) *Mol. Cell Biol.* 62:109–120).

Antibodies may also be produced by inducing in vivo production in the lymphocyte population or by screening immunoglobulin libraries or panels of highly specific binding reagents as disclosed in the literature (Orlandi, R. et al. (1989) *Proc. Natl. Acad Sci.* 86: 3833–3837; Winter, G. et al. (1991) *Nature* 349:293–299).

Antibody fragments which contain specific binding sites for proteins of the invention may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse, W. D. et al. (1989) *Science* 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between a protein of the invention and its specific antibody.

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Kits for determining if a sample contains proteins of the present invention will include at least one reagent specific for detecting the presence or absence of the protein. Diagnostic kits for carrying out antibody assays may be produced in a number of ways. In one embodiment, the diagnostic kit comprises (a) an antibody which binds proteins of the present invention conjugated to a solid support and (b) a second antibody which binds proteins of the present invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as above, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

Binding proteins or peptides other than antibodies, and binding compounds other than proteins or peptides, can be identified by screening combinatorial libraries of such compounds with the screening assays described below.

5. Screening Assays

As noted above, the present invention provides methods of screening a compound for the ability to disrupt plant parasitic nematode feeding and/or chemotaxis. The methods comprise determining whether or not that compound selectively binds to a nematode guanylyl cyclase chemoreceptor protein encoded by a DNA as described herein. The presence of such binding indicates the compound is useful in disrupting plant parasitic nematode feeding and/or chemotaxis. The determining step may be carried out in vitro with a cell membrane preparation containing the proteins produced from recombinant cells as described above, or even in a membrane-free preparation. Alternatively, the determining step may be carried out in vivo in a cell culture comprising cells that express the protein, in accordance with known techniques.

The compound screened may be a member of a combinatorial library, which generally are comprised of non-oligomers, oligomers, or combinations thereof. Non-oligomer combinatorial libraries include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, terpenes, porphyrins, toxins, catalysts, as well as combinations thereof.

Oligomer combinatorial libraries include oligopeptides, oligonucleotides, oligosaccharides, polylipids, polyesters, polyamides, polyurethanes, polyureas, polyethers, and poly (phosphorus derivatives), e.g. phosphates, phosphonates, phosphoramides, phosphonamides, phosphites, phosphinamides, etc., poly (sulfur derivatives) e.g., sulfones, sulfonates, sulfites, sulfonamides, sulfenamides, etc., where for the phosphorous and sulfur derivatives the indicated heteroatom for the most part will be bonded to C,H,N,O or S, and combinations thereof.

When the compound to be screened is a member of a combinatorial library, the screening step may be incorporated into a high throughput screening procedure in accordance with known techniques. In this case, the members of the combinatorial library may be immobilized on solid supports, which solid supports may be separate from one another (e.g, particles or beads) as described in U.S. Pat. No. 5,656,324 to Still et al., or may be discrete regions on a surface portion of a unitary substrate. Such "chip-type" or "pin-type" solid supports are known. See, e.g., U.S. Pat. No. 5,288,514 to Ellman (pin-based support); U.S. Pat. No. 5,510,270 to Fodor et al. (chip-based support). In addition, the screening step may be carried out with any other suitable combinatorial library technique, including but not limited to phage display. See, e.g., U.S. Pat. No. 5,812,047 to Garrard et al.; U.S. Pat. No. 5,223,409 to Ladner et al.; U.S. Pat. No. 5,498,538 to Kay & Fowlkes; U.S. Pat. No. 4,953,002 to Dulbecco.

One of the principal assays to determine efficacy of potential inhibitors of chemosensory receptors will be to transform plant cells and tissues with genes encoding chemosensory inhibitor molecules (like those mentioned in this application, preferably peptides) and test their effect on nematode chemotaxis. Expression of cassettes producing encoded inhibitory molecules that may be retained, or preferably designed to be exuded from plant tissues (i.e. roots), may be under the control of constitutive promoters such as CaMV 35S, Ro1A-D, nopaline synthase, gamma-TIP, T-cyt, and TR2', or inducible promoters such as those derived from expressed plant genes like TobRB7, cdc2At, and wun1 (H. Atkinson et al., in The Physiology and Biochemistry of Free-Living and Plant-Parasitic Nematodes, pp. 382–413 (ed. R N Perry, D J Wright, 1998); G. Gheysen et al., in *Cellular and Molecular Aspects of Plant-Nematode Interactions*, pp. 120–132 (ed. C Fenoll, F M W Grundler, SA Oh1, 1997); A. Goverse et al., *Physiol. Mol. Plant Pathol.* 52:275–284 (1998)). Transformation of plant cells and tissues may be conducted using Agrobacterium tumefascians, Agrobacterium rhizogenes, or biolistic approaches (Atkinson et al., 1998). Transformation of plant roots via A. rhizogenes is preferable for screening purposes since these systems work in many plant species and have been demonstrated to produce a reproducible and scorable plant-nematode interaction (D. Cai et al., *Science* 275, 832–834 (1997); M. Savka et al., *Phytopathology* 80, 503–508 (1990)). A variety of agar and soil-based assays may be utilized to. assess the effect of transgenic expression of chemosensory inhibitors in plants on nematode chemotactic ability (C. Bargmann and I. Mori. Chemotaxis and thermotaxis. Pp. 717–737 In Riddle, D. L., T. Blumenthal, B. J. Meyer, and J. R. Priess, eds., C. elegans II, (Cold Spring Harbor Laboratory Press, NY 1997)).

6. Antisense Oligonucleotides and Double-stranded RNA

Antisense oligonucleotides. The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

Antisense oligonucleotides and nucleic acids that express the same may be made in accordance with conventional techniques. See, e.g., U.S. Pat. No. 5,023,243 to Tullis; U.S. Pat. No. 5,149,797 to Pederson et al. The length of the antisense oligonucleotide (i.e., the number of nucleotides therein) is not critical so long as it binds selectively to the intended location, and can be determined in accordance with routine procedures. In general, the antisense oligonucleotide will be from 8, 10 or 12 nucleotides in length up to 20, 30, or 50 nucleotides in length. Such antisense oligonucleotides may be oligonucleotides wherein at least one, or all, or the intemucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues may be modified as described. In another non-limiting example, such antisense oligonucleotides are oligonucleotides wherein at least one, or all, of the nucleotides contain a 2' loweralkyl moiety (e.g., $C_1$–$C_4$, linear or branched, saturated or unsaturated alkyl, such as methyl, ethyl, ethenyl, propyl, 1-propenyl, 2-propenyl, and isopropyl). For example, every other one of the nucleotides may be modified as described. See also P. Furdon et al., *Nucleic Acids Res.* 17, 9193–9204 (1989); S. Agrawal et al., *Proc. Natl. Acad. Sci. USA* 87, 1401–405 (1990); C. Baker et al., *Nucleic Acids Res.* 18, 3537–3543 (1990); B. Sproat et al., *Nucleic Acids Res.* 17, 3373–3386 (1989); R. Walder and J. Walder, *Proc. Natl. Acad Sci. USA* 85, 5011–5015 (1988).

Antisense oligonucleotides may be used as biological control agents per se, or DNA encoding such antisense oligonucleotides may be provided in an expression cassette which is capable of infecting a host nematode and transforming cells of the same, which expression cassette may in turn be used as a biological control agent.

RNA interference (RNAi). RNAi is a methodology to directly inhibit gene activity that is both powerful and efficient is the double-stranded (ds) RNA-mediated interference (RNAi) of gene expression as demonstrated in C. elegans (A. Fire et al., Potent and specific genetic interference by double-stranded RNA in Caenorhabditis elegans, *Nature* 391, 806–11 (1998); L. Timmons and A. Fire, Specific interference by ingested dsRNA. *Nature* 395, 854 (1998)). In this methodology, dsRNA complementary to a gene-of-interest (in this case, a DNA as described above) is administered to (e.g., injected into or ingested by) the target nematode. As a consequence, activity of the gene-of-interest is transiently abolished in the treated animal. Thus such agents are useful in the control of nematodes as described above. Two distinct advantages provided by RNAi analyses include; the dsRNA does not have to be injected into the nematode germ line to exert inhibitory effects in tissues distal to the injection site (i. e. RNAi does not require successful transformation); and the inhibitory effects of injected dsRNA can be realized in one or more subsequent nematode generations derived from the treated parent. RNAi designed to knock-out gene function in nematodes can be assayed directly for its effects on chemosensory behavior. It also will be important to monitor the effects RNAi by mRNA in situ hybridization and/or antibody probes to the target gene product to confirm inhibition. The dsRNA is, in general, from 8, 10 or 12 nucleotides in length up to 20, 30, or 50 nucleotides in length, each strand (although the strands do not have to be identical in length).

7. Control of Plant Parasitic Nematodes

The present invention provides a variety of means for controlling plant parasitic nematodes, as described above.

Nematodes may be administered an expression cassette that contains and expresses a DNA as described thereof, or a fragment thereof of a length sufficient to induce silencing (e.g., at least partial silencing) of expression of the guanylyl cyclase chemoreceptor in the nematode, and thereby disrupt feeding or chemotaxis of the nematode.

Nematodes may be administered an antisense oligonucleotide as described above, either per se or through a vector that expresses the antisense oligonucleotide, in an amount sufficient to disrupt feeding or chemotaxis of the nematode.

Nematodes may be administered an oligonucleotide as described above (such as an RNAi oligonucleotide as described above) in an amount sufficient to disrupt feeding or chemotaxis of the nematode.

Nematodes may be administered a protein or peptide (e.g., an antibody) that specifically binds to the guanylyl cyclase chemoreceptor proteins disclosed hereinabove, in an amount sufficient to disrupt the feeding or chemotaxis of the nematode. Such proteins and peptides, including antibodies, are readily produced in the manner described above.

Administration of the active compounds described above may be by any suitable means, such as by spraying crops or plants with the active agents described above, by treating soil with the active agents described above, etc. The active agents may be combined with a suitable agricultural carrier, including aqueous carriers, nonaqueous carriers, emulsions, dry powders, etc., which may optionally include stickers, adjuvants and the like, all in accordance with standard techniques, with the active agent being included in any suitable amount (e.g., from 0.001 to 99 percent by weight of the total composition).

The present invention is explained in greater detail in the following non-limiting Examples.

EXAMPLE 1

Identification of HG-gcy-1

The soybean cyst nematode (SCN), *Heterodera glycines* guanylyl cyclase-1 (HG-gcy-1) coding sequence was first located by the instant inventors about 1 kb upstream of β-1,4-endoglucanase-1 precursor during a study of the organization of β-1,4-endoglucanase gene family in the soybean cyst nematode. The full-length chemosensory guanylyl cyclase gene HG-gcy-1 was generated by further Lambda genomic clone mapping, oligo(dT) cDNA library screening and 5'RACE. A partial cDNA clone of Hg-gcy-1 was obtained by screening a SCN cDNA library and the partial HG-gcy-1 cDNA sequence was released in GenBank on Nov. 9, 1998 (GenBank accession number AF095746). The HG-gcy-1 full-length cDNA sequence (3762 bp) (SEQ ID NO: 1) was released in GenBank on Mar. 5, 1999 with an accession number (AF095746).

By comparing the HG-gcy-1 genomic sequence (SEQ ID NO: 3) and cDNA sequence, 24 introns were identified in HG-gcy-1 gene. The predicted protein of HG-gcy-1 (SEQ ID NO: 2) had strong homology to a family of guanylyl cyclase chemoreceptors reported in the nematode *Caenorhabditis elegans*. We have recently localized transcripts of HG-gcy-1 in SCN chemosensory cells by mRNA in situ hybridization (data not reported).

EXAMPLE 2

Identification of HG-gcy-2 and HG-gcy-3

A DNA DIG labeled probe was synthesized based on the guanylyl cyclase catalytic domain sequence. The primers used to synthesize the probe was cycleExp3 and cycleExp4. The cycleExp3 primer sequence is:

AGCGGATCCCGTCCGCGCATGGACATTGTG (SEQ ID NO: 8).

The cycleExp4 prime sequence is:

CCGCTCGAGCGTTGCGGCACTCGCATTTCT (SEQ ID NO: 9)

The thus synthesized DNA probe was used to screen the SCN oligo(dT) cDNA library with both hybridization and washing temperature at 65° C. This endeavor lead to the identification of two additional guanylyl cyclase genes, namely HG-gcy-2 (3499 bps) (SEQ ID NO: 4) (the protein fragment being given as SEQ ID NO: 5) and HG-gcy-3 (3007 bps) (SEQ ID NO: 6) (the protein fragment being given as SEQ ID NO: 7). These sequences may be elongated in accordance with known techniques to provide the full length sequences thereof.

SEQUENCE LISTING

```
<160> NUMBER OF SEQ ID NOS: 9

<210> SEQ ID NO 1
<211> LENGTH: 3762
<212> TYPE: DNA
<213> ORGANISM: Heterodera glycines
<220> FEATURE:
<221> NAME/KEY: CDS
<222> LOCATION: (78)..(3533)

<400> SEQUENCE: 1

gggatttgaa tcccgacaaa tcgccttttt aatgaattca tttcatttta aaatttcctt      60

gcccaaaatc tctcaaa atg gaa atg ccg tcc tgt ttc ttc ctc ctt ttc        110
                   Met Glu Met Pro Ser Cys Phe Phe Leu Leu Phe
                     1               5                  10

ttt ctt atg ctt ttt gtc agc cct tct cgg cac caa tta gtc act gtt        158
Phe Leu Met Leu Phe Val Ser Pro Ser Arg His Gln Leu Val Thr Val
            15                  20                  25

agc aac tca tcg tct tcg ccc att ggc acc acc gtc gct ttt ggc act        206
Ser Asn Ser Ser Ser Ser Pro Ile Gly Thr Thr Val Ala Phe Gly Thr
        30                  35                  40

cct tcg ccg atc atc cca atc tct act gca ccc tcc acg aat ggc act        254
Pro Ser Pro Ile Ile Pro Ile Ser Thr Ala Pro Ser Thr Asn Gly Thr
    45                  50                  55

gcc act ttt ggc gtc cct ccg ccg atc agt ccg ccg att aat tct tcg        302
Ala Thr Phe Gly Val Pro Pro Pro Ile Ser Pro Pro Ile Asn Ser Ser
 60                  65                  70                  75
```

-continued

```
tcc tct ctc cca tca act ggt cct ttg gaa gca tcg gtt cag tta aaa      350
Ser Ser Leu Pro Ser Thr Gly Pro Leu Glu Ala Ser Val Gln Leu Lys
                 80                  85                  90

atc ggc ttc ctc ttt gct aac ggc acc caa cgg ttg cga atg ctt ttc      398
Ile Gly Phe Leu Phe Ala Asn Gly Thr Gln Arg Leu Arg Met Leu Phe
             95                 100                 105

ggc ttt ggc caa tcc gcg ccc gcc gtc act ttg gca ctc gaa cgg gcg      446
Gly Phe Gly Gln Ser Ala Pro Ala Val Thr Leu Ala Leu Glu Arg Ala
        110                 115                 120

agg cag gag cac ctc atc gac agc atc aac ttc act tac acg tgg cga      494
Arg Gln Glu His Leu Ile Asp Ser Ile Asn Phe Thr Tyr Thr Trp Arg
    125                 130                 135

atg tgc ggc tgc ttt cag cct tgg gct gtc ggc tac gcc act caa ctg      542
Met Cys Gly Cys Phe Gln Pro Trp Ala Val Gly Tyr Ala Thr Gln Leu
140                 145                 150                 155

gtt ctg acg gaa aat gtg gac gct ttg atc ggt ccg cct tgt gcc atc      590
Val Leu Thr Glu Asn Val Asp Ala Leu Ile Gly Pro Pro Cys Ala Ile
                160                 165                 170

gcc gcg gga tac gtg gcc tcc ttc tac aac att cca ctg tat ttg tgg      638
Ala Ala Gly Tyr Val Ala Ser Phe Tyr Asn Ile Pro Leu Tyr Leu Trp
            175                 180                 185

ggt gct act gtg gcc tcg gaa ttt tac aac act acc gta tac cct aca      686
Gly Ala Thr Val Ala Ser Glu Phe Tyr Asn Thr Thr Val Tyr Pro Thr
        190                 195                 200

ctg aac aac gtg aac gtt aac tcg gac atg ttg gcg ttg gcc tta caa      734
Leu Asn Asn Val Asn Val Asn Ser Asp Met Leu Ala Leu Ala Leu Gln
    205                 210                 215

agt gtg ttg gtg caa ttc aat tgg aca gaa gtg tcc ttc gtg tac act      782
Ser Val Leu Val Gln Phe Asn Trp Thr Glu Val Ser Phe Val Tyr Thr
220                 225                 230                 235

ccg gac aat gag cga atg gtc tgt aac tcg gtg aaa cag agt ctc aca      830
Pro Asp Asn Glu Arg Met Val Cys Asn Ser Val Lys Gln Ser Leu Thr
                240                 245                 250

aat gtg ctc aac gtg acc aat gtg acc att gtt ttc cag cat cag atg      878
Asn Val Leu Asn Val Thr Asn Val Thr Ile Val Phe Gln His Gln Met
            255                 260                 265

gag tcc aat gtg gac agt atg aag gcg acg ctg aga aat ctg cgc agc      926
Glu Ser Asn Val Asp Ser Met Lys Ala Thr Leu Arg Asn Leu Arg Ser
        270                 275                 280

cga tcg cga att gtg ctt tcc tgt ttc gat gtc gag gtt gac cgt cgc      974
Arg Ser Arg Ile Val Leu Ser Cys Phe Asp Val Glu Val Asp Arg Arg
    285                 290                 295

aac ttt ctg ttg tcc att ttc gac act ggt ctt gct gcg gac aac gaa     1022
Asn Phe Leu Leu Ser Ile Phe Asp Thr Gly Leu Ala Ala Asp Asn Glu
300                 305                 310                 315

ttt gtg ttc atc atg gga tcc ctg cgc aac cag ggc atg ctc cag cag     1070
Phe Val Phe Ile Met Gly Ser Leu Arg Asn Gln Gly Met Leu Gln Gln
                320                 325                 330

gtt gcg tcg cgt gag gac ggc agt gtc aaa tat gtg aac aat tgg atg     1118
Val Ala Ser Arg Glu Asp Gly Ser Val Lys Tyr Val Asn Asn Trp Met
            335                 340                 345

gac aaa aac agc cca ggc gat ggc cgc gac tcg gac gca ctc gcc gcg     1166
Asp Lys Asn Ser Pro Gly Asp Gly Arg Asp Ser Asp Ala Leu Ala Ala
        350                 355                 360

aca aaa cac gtc ata atg att gac ctg gaa aac caa tcg agt gat cat     1214
Thr Lys His Val Ile Met Ile Asp Leu Glu Asn Gln Ser Ser Asp His
    365                 370                 375

ctt aac gaa ttc aac cga gat ttg agt gcg aaa ttc ggc act tat ccc     1262
Leu Asn Glu Phe Asn Arg Asp Leu Ser Ala Lys Phe Gly Thr Tyr Pro
```

-continued

```
            380                 385                 390                 395
ttt ttc tgc aac gga agt tgc atg ggc ggc gca gca gaa caa tcg ccg      1310
Phe Phe Cys Asn Gly Ser Cys Met Gly Gly Ala Ala Glu Gln Ser Pro
                400                 405                 410

tcg caa tac gcc agg gct ttg ttc gac aca aca tac gca tat ttt aga      1358
Ser Gln Tyr Ala Arg Ala Leu Phe Asp Thr Thr Tyr Ala Tyr Phe Arg
            415                 420                 425

gca ttg aat cgc aca atg gaa aag cgc aaa tcg aat ggg agg gat ttg      1406
Ala Leu Asn Arg Thr Met Glu Lys Arg Lys Ser Asn Gly Arg Asp Leu
            430                 435                 440

ttg cgc aac ggc acg gaa ttg aac gca gaa act gcc ggg acg acc ttt      1454
Leu Arg Asn Gly Thr Glu Leu Asn Ala Glu Thr Ala Gly Thr Thr Phe
            445                 450                 455

cag ggc gag acc gga cgc atc act ttt gac gcc cac ggc aac cgc cag      1502
Gln Gly Glu Thr Gly Arg Ile Thr Phe Asp Ala His Gly Asn Arg Gln
460                 465                 470                 475

ccg acc ttt ttt gtg acg atg cta aac gca ctg aat gtg ccc act gtt      1550
Pro Thr Phe Phe Val Thr Met Leu Asn Ala Leu Asn Val Pro Thr Val
            480                 485                 490

atg gtg aaa gtg aac att acc aac gga gta ttg aaa atg gaa cgg ctg      1598
Met Val Lys Val Asn Ile Thr Asn Gly Val Leu Lys Met Glu Arg Leu
            495                 500                 505

tac ggc agt gag gcg tcg ctg tgg gtc aat tgg ggc ggc ttt cgg ccg      1646
Tyr Gly Ser Glu Ala Ser Leu Trp Val Asn Trp Gly Gly Phe Arg Pro
            510                 515                 520

atg acc acg ccg ttg tgc ggc tac aac ggc aca atg tgt ggc caa aat      1694
Met Thr Thr Pro Leu Cys Gly Tyr Asn Gly Thr Met Cys Gly Gln Asn
            525                 530                 535

gtg acg gtg tac att ctg atc ggc gtt acg ctt atg ttg ctg ttg ctg      1742
Val Thr Val Tyr Ile Leu Ile Gly Val Thr Leu Met Leu Leu Leu Leu
540                 545                 550                 555

gtc gcc gct ttg ctt ggc atc gga tac gca att cgg gag aaa atg cgc      1790
Val Ala Ala Leu Leu Gly Ile Gly Tyr Ala Ile Arg Glu Lys Met Arg
            560                 565                 570

gag aag cag cgc ctg aca cgc gag tgt ttg atc cca ttt gca gag ctg      1838
Glu Lys Gln Arg Leu Thr Arg Glu Cys Leu Ile Pro Phe Ala Glu Leu
            575                 580                 585

cgc aac ctg aaa gag ctg cgc agt tcg gag gaa ctg aag tcg gag acg      1886
Arg Asn Leu Lys Glu Leu Arg Ser Ser Glu Glu Leu Lys Ser Glu Thr
            590                 595                 600

gag aag agc atg cgg agc atg cgt agc agt cag tcg gga agc aca cgg      1934
Glu Lys Ser Met Arg Ser Met Arg Ser Ser Gln Ser Gly Ser Thr Arg
            605                 610                 615

ctt acg gtc ggc agc cac aaa gcg cag cgg gag acg gcc aat tgc gcg      1982
Leu Thr Val Gly Ser His Lys Ala Gln Arg Glu Thr Ala Asn Cys Ala
620                 625                 630                 635

ttc ttt gtg ttc aac cgg gaa att gtg ctg gcc gtg aaa tac cac gtc      2030
Phe Phe Val Phe Asn Arg Glu Ile Val Leu Ala Val Lys Tyr His Val
            640                 645                 650

agg gtg cga att atg tcc gaa gat ttg gcc ttc att agg aag ctg cgg      2078
Arg Val Arg Ile Met Ser Glu Asp Leu Ala Phe Ile Arg Lys Leu Arg
            655                 660                 665

cag ttg gac cac gac aac atg aac aag ttg tac ggc gtg tgc acc gat      2126
Gln Leu Asp His Asp Asn Met Asn Lys Leu Tyr Gly Val Cys Thr Asp
            670                 675                 680

ggg ccc ctt ttg ttc gca att tgg cgc aat tgt cag cga ggg aca tta      2174
Gly Pro Leu Leu Phe Ala Ile Trp Arg Asn Cys Gln Arg Gly Thr Leu
            685                 690                 695

aaa gaa ctg atc gcc aag gag caa tac gtt ggg gac aat tgt gtg atg      2222
```

-continued

```
Lys Glu Leu Ile Ala Lys Glu Gln Tyr Val Gly Asp Asn Cys Val Met
700                 705                 710                 715

ttt gct ctg atg cgg gac att gca aat ggt ctg ctc gcc atc cat caa      2270
Phe Ala Leu Met Arg Asp Ile Ala Asn Gly Leu Leu Ala Ile His Gln
                720                 725                 730

tcg ttc atc gga gcc cac ggg ctg ctc tcc tct gaa aat tgt ctg atc      2318
Ser Phe Ile Gly Ala His Gly Leu Leu Ser Ser Glu Asn Cys Leu Ile
            735                 740                 745

aat gac cgg tgg caa gtg aaa atc agc gac ttt ggc ctg aat atg atc      2366
Asn Asp Arg Trp Gln Val Lys Ile Ser Asp Phe Gly Leu Asn Met Ile
        750                 755                 760

aga gaa agt caa acg ctg tcg aag aaa gca ctt ttg tgg acg gcg cct      2414
Arg Glu Ser Gln Thr Leu Ser Lys Lys Ala Leu Leu Trp Thr Ala Pro
    765                 770                 775

gaa ctt ttg cga gaa aac aat cgg aag gga gca aaa gag ggc gat gtg      2462
Glu Leu Leu Arg Glu Asn Asn Arg Lys Gly Ala Lys Glu Gly Asp Val
780                 785                 790                 795

ttc agt ttt gcg atc att tgt gtg gaa atg atg aac aga gag acg gtg      2510
Phe Ser Phe Ala Ile Ile Cys Val Glu Met Met Asn Arg Glu Thr Val
                800                 805                 810

tgg aac gga gtg gaa agg gac caa gac atc gat gaa atc ctt tat cgg      2558
Trp Asn Gly Val Glu Arg Asp Gln Asp Ile Asp Glu Ile Leu Tyr Arg
            815                 820                 825

ctc aga cgc acc aac acc aca atc cct cac cgt ccg cag ctt cat ccc      2606
Leu Arg Arg Thr Asn Thr Thr Ile Pro His Arg Pro Gln Leu His Pro
        830                 835                 840

cgc gca gag att aac caa agt ttg ctt cat ctg atc aga gac tgt tgg      2654
Arg Ala Glu Ile Asn Gln Ser Leu Leu His Leu Ile Arg Asp Cys Trp
    845                 850                 855

tcc gaa gtg ccg tcc gaa cgt ccg cgc atg gac att gtg cga acg atg      2702
Ser Glu Val Pro Ser Glu Arg Pro Arg Met Asp Ile Val Arg Thr Met
860                 865                 870                 875

ctc aaa cag atg gtc cag gac ggc agt caa aat ctg atg gat tac gtg      2750
Leu Lys Gln Met Val Gln Asp Gly Ser Gln Asn Leu Met Asp Tyr Val
                880                 885                 890

ttc ggc atg ttg gag cag tac gcg agt tcg ctg gag cag gag gtg gag      2798
Phe Gly Met Leu Glu Gln Tyr Ala Ser Ser Leu Glu Gln Glu Val Glu
            895                 900                 905

gaa cgg acc aaa gag ttg gtg gag gag aag cgc aag agc gac att ctt      2846
Glu Arg Thr Lys Glu Leu Val Glu Glu Lys Arg Lys Ser Asp Ile Leu
        910                 915                 920

ctc tac cgg atg ttg ccg cgg cag gtg gcg gac aaa ctg aag ata ggc      2894
Leu Tyr Arg Met Leu Pro Arg Gln Val Ala Asp Lys Leu Lys Ile Gly
    925                 930                 935

gag tct gtg gag cca gaa tcc ttc caa atg gcc acc att ttc ttc tcc      2942
Glu Ser Val Glu Pro Glu Ser Phe Gln Met Ala Thr Ile Phe Phe Ser
940                 945                 950                 955

gac gtc gtc tcc ttc acc act ttg gcc ggc aaa tgc tcg cca ttg caa      2990
Asp Val Val Ser Phe Thr Thr Leu Ala Gly Lys Cys Ser Pro Leu Gln
                960                 965                 970

gtt gtg aat ctg ctc aac ggt ctg ttc aca gcc ttt gac ggg atc att      3038
Val Val Asn Leu Leu Asn Gly Leu Phe Thr Ala Phe Asp Gly Ile Ile
            975                 980                 985

gac act cat gac tgc tac aaa gtt gaa acc att ggc gat ggc tat ttg      3086
Asp Thr His Asp Cys Tyr Lys Val Glu Thr Ile Gly Asp Gly Tyr Leu
        990                 995                1000

gtc tgt tcg ggc att ccg aag cgc aac ggc gac caa cac gcg aaa gaa      3134
Val Cys Ser Gly Ile Pro Lys Arg Asn Gly Asp Gln His Ala Lys Glu
   1005                1010                1015
```

-continued

```
ata gcc gaa ctt tcg ttc gcc ttc ctt cgc act gtg tcc agc ttc cgt     3182
Ile Ala Glu Leu Ser Phe Ala Phe Leu Arg Thr Val Ser Ser Phe Arg
1020                1025                1030                1035

gtc gat cac ctc ccc tcc gaa cgg gtc aac ctt cgc att ggc ttc cat     3230
Val Asp His Leu Pro Ser Glu Arg Val Asn Leu Arg Ile Gly Phe His
               1040                1045                1050

tcc gga cca gcg gtc gct ggc gtc gtc gga ctg aca atg ccg cgc tat     3278
Ser Gly Pro Ala Val Ala Gly Val Val Gly Leu Thr Met Pro Arg Tyr
           1055                1060                1065

tgt ctc ttt ggg gac tca gtg aac acg gcc agc cga atg gag tca aac     3326
Cys Leu Phe Gly Asp Ser Val Asn Thr Ala Ser Arg Met Glu Ser Asn
       1070                1075                1080

gga aag gca ggc cga gtg cac att tca tca agt gcc aac cac ttt ttg     3374
Gly Lys Ala Gly Arg Val His Ile Ser Ser Ser Ala Asn His Phe Leu
   1085                1090                1095

acc agt gta atc ggc gga tat gtg aca gag cca aga ggc gaa gtg att     3422
Thr Ser Val Ile Gly Gly Tyr Val Thr Glu Pro Arg Gly Glu Val Ile
1100                1105                1110                1115

ata aag ggc aaa gga gtg atg gag acc ttt tgg ctg tta ggg cga att     3470
Ile Lys Gly Lys Gly Val Met Glu Thr Phe Trp Leu Leu Gly Arg Ile
               1120                1125                1130

gga gag gca cat ttg tcg gag ggc aca gcg gaa aga aat gcg agt gcc     3518
Gly Glu Ala His Leu Ser Glu Gly Thr Ala Glu Arg Asn Ala Ser Ala
           1135                1140                1145

gca acg aga aaa tga agaaacatca cacggcattc cctctgatca ctcattttaa     3573
Ala Thr Arg Lys
       1150

tgactcgaaa tcattgacca attttaatga attttaatct cttttattat tatgatagcg   3633

caatttttgc gcacatttaa gcgataacaa tttttatatt aaagttcccc ttaacaaatt   3693

tactattgta aatactgtct cgaatacaaa aaatgtataa tttactatta aaaaaaaaaa   3753

aaaaaaaaa                                                           3762


<210> SEQ ID NO 2
<211> LENGTH: 1151
<212> TYPE: PRT
<213> ORGANISM: Heterodera glycines

<400> SEQUENCE: 2

Met Glu Met Pro Ser Cys Phe Phe Leu Leu Phe Phe Leu Met Leu Phe
  1               5                  10                  15

Val Ser Pro Ser Arg His Gln Leu Val Thr Val Ser Asn Ser Ser Ser
             20                  25                  30

Ser Pro Ile Gly Thr Thr Val Ala Phe Gly Thr Pro Ser Pro Ile Ile
         35                  40                  45

Pro Ile Ser Thr Ala Pro Ser Thr Asn Gly Thr Ala Thr Phe Gly Val
     50                  55                  60

Pro Pro Pro Ile Ser Pro Pro Ile Asn Ser Ser Ser Ser Leu Pro Ser
 65                  70                  75                  80

Thr Gly Pro Leu Glu Ala Ser Val Gln Leu Lys Ile Gly Phe Leu Phe
                 85                  90                  95

Ala Asn Gly Thr Gln Arg Leu Arg Met Leu Phe Gly Phe Gly Gln Ser
            100                 105                 110

Ala Pro Ala Val Thr Leu Ala Leu Glu Arg Ala Arg Gln Glu His Leu
        115                 120                 125

Ile Asp Ser Ile Asn Phe Thr Tyr Thr Trp Arg Met Cys Gly Cys Phe
    130                 135                 140
```

-continued

```
Gln Pro Trp Ala Val Gly Tyr Ala Thr Gln Leu Val Leu Thr Glu Asn
145                 150                 155                 160

Val Asp Ala Leu Ile Gly Pro Pro Cys Ala Ile Ala Ala Gly Tyr Val
                165                 170                 175

Ala Ser Phe Tyr Asn Ile Pro Leu Tyr Leu Trp Gly Ala Thr Val Ala
            180                 185                 190

Ser Glu Phe Tyr Asn Thr Thr Val Tyr Pro Thr Leu Asn Asn Val Asn
        195                 200                 205

Val Asn Ser Asp Met Leu Ala Leu Ala Leu Gln Ser Val Leu Val Gln
    210                 215                 220

Phe Asn Trp Thr Glu Val Ser Phe Val Tyr Thr Pro Asp Asn Glu Arg
225                 230                 235                 240

Met Val Cys Asn Ser Val Lys Gln Ser Leu Thr Asn Val Leu Asn Val
                245                 250                 255

Thr Asn Val Thr Ile Val Phe Gln His Gln Met Glu Ser Asn Val Asp
            260                 265                 270

Ser Met Lys Ala Thr Leu Arg Asn Leu Arg Ser Arg Ser Arg Ile Val
        275                 280                 285

Leu Ser Cys Phe Asp Val Glu Val Asp Arg Arg Asn Phe Leu Leu Ser
    290                 295                 300

Ile Phe Asp Thr Gly Leu Ala Ala Asp Asn Glu Phe Val Phe Ile Met
305                 310                 315                 320

Gly Ser Leu Arg Asn Gln Gly Met Leu Gln Gln Val Ala Ser Arg Glu
                325                 330                 335

Asp Gly Ser Val Lys Tyr Val Asn Asn Trp Met Asp Lys Asn Ser Pro
            340                 345                 350

Gly Asp Gly Arg Asp Ser Asp Ala Leu Ala Ala Thr Lys His Val Ile
        355                 360                 365

Met Ile Asp Leu Glu Asn Gln Ser Ser Asp His Leu Asn Glu Phe Asn
    370                 375                 380

Arg Asp Leu Ser Ala Lys Phe Gly Thr Tyr Pro Phe Phe Cys Asn Gly
385                 390                 395                 400

Ser Cys Met Gly Gly Ala Ala Glu Gln Ser Pro Ser Gln Tyr Ala Arg
                405                 410                 415

Ala Leu Phe Asp Thr Thr Tyr Ala Tyr Phe Arg Ala Leu Asn Arg Thr
            420                 425                 430

Met Glu Lys Arg Lys Ser Asn Gly Arg Asp Leu Leu Arg Asn Gly Thr
        435                 440                 445

Glu Leu Asn Ala Glu Thr Ala Gly Thr Thr Phe Gln Gly Glu Thr Gly
    450                 455                 460

Arg Ile Thr Phe Asp Ala His Gly Asn Arg Gln Pro Thr Phe Phe Val
465                 470                 475                 480

Thr Met Leu Asn Ala Leu Asn Val Pro Thr Val Met Val Lys Val Asn
                485                 490                 495

Ile Thr Asn Gly Val Leu Lys Met Glu Arg Leu Tyr Gly Ser Glu Ala
            500                 505                 510

Ser Leu Trp Val Asn Trp Gly Gly Phe Arg Pro Met Thr Thr Pro Leu
        515                 520                 525

Cys Gly Tyr Asn Gly Thr Met Cys Gly Gln Asn Val Thr Val Tyr Ile
    530                 535                 540

Leu Ile Gly Val Thr Leu Met Leu Leu Leu Leu Val Ala Ala Leu Leu
545                 550                 555                 560

Gly Ile Gly Tyr Ala Ile Arg Glu Lys Met Arg Glu Lys Gln Arg Leu
```

-continued

```
            565                 570                 575

Thr Arg Glu Cys Leu Ile Pro Phe Ala Glu Leu Arg Asn Leu Lys Glu
        580                 585                 590

Leu Arg Ser Ser Glu Glu Leu Lys Ser Glu Thr Glu Lys Ser Met Arg
    595                 600                 605

Ser Met Arg Ser Ser Gln Ser Gly Ser Thr Arg Leu Thr Val Gly Ser
    610                 615                 620

His Lys Ala Gln Arg Glu Thr Ala Asn Cys Ala Phe Phe Val Phe Asn
625                 630                 635                 640

Arg Glu Ile Val Leu Ala Val Lys Tyr His Val Arg Val Arg Ile Met
            645                 650                 655

Ser Glu Asp Leu Ala Phe Ile Arg Lys Leu Arg Gln Leu Asp His Asp
        660                 665                 670

Asn Met Asn Lys Leu Tyr Gly Val Cys Thr Asp Gly Pro Leu Leu Phe
    675                 680                 685

Ala Ile Trp Arg Asn Cys Gln Arg Gly Thr Leu Lys Glu Leu Ile Ala
    690                 695                 700

Lys Glu Gln Tyr Val Gly Asp Asn Cys Val Met Phe Ala Leu Met Arg
705                 710                 715                 720

Asp Ile Ala Asn Gly Leu Leu Ala Ile His Gln Ser Phe Ile Gly Ala
            725                 730                 735

His Gly Leu Leu Ser Ser Glu Asn Cys Leu Ile Asn Asp Arg Trp Gln
        740                 745                 750

Val Lys Ile Ser Asp Phe Gly Leu Asn Met Ile Arg Glu Ser Gln Thr
    755                 760                 765

Leu Ser Lys Lys Ala Leu Leu Trp Thr Ala Pro Glu Leu Leu Arg Glu
    770                 775                 780

Asn Asn Arg Lys Gly Ala Lys Glu Gly Asp Val Phe Ser Phe Ala Ile
785                 790                 795                 800

Ile Cys Val Glu Met Met Asn Arg Glu Thr Val Trp Asn Gly Val Glu
            805                 810                 815

Arg Asp Gln Asp Ile Asp Glu Ile Leu Tyr Arg Leu Arg Arg Thr Asn
        820                 825                 830

Thr Thr Ile Pro His Arg Pro Gln Leu His Pro Arg Ala Glu Ile Asn
    835                 840                 845

Gln Ser Leu Leu His Leu Ile Arg Asp Cys Trp Ser Glu Val Pro Ser
    850                 855                 860

Glu Arg Pro Arg Met Asp Ile Val Arg Thr Met Leu Lys Gln Met Val
865                 870                 875                 880

Gln Asp Gly Ser Gln Asn Leu Met Asp Tyr Val Phe Gly Met Leu Glu
            885                 890                 895

Gln Tyr Ala Ser Ser Leu Glu Gln Glu Val Glu Glu Arg Thr Lys Glu
        900                 905                 910

Leu Val Glu Glu Lys Arg Lys Ser Asp Ile Leu Leu Tyr Arg Met Leu
    915                 920                 925

Pro Arg Gln Val Ala Asp Lys Leu Lys Ile Gly Glu Ser Val Glu Pro
    930                 935                 940

Glu Ser Phe Gln Met Ala Thr Ile Phe Phe Ser Asp Val Val Ser Phe
945                 950                 955                 960

Thr Thr Leu Ala Gly Lys Cys Ser Pro Leu Gln Val Val Asn Leu Leu
            965                 970                 975

Asn Gly Leu Phe Thr Ala Phe Asp Gly Ile Ile Asp Thr His Asp Cys
        980                 985                 990
```

-continued

```
Tyr Lys Val Glu Thr Ile Gly Asp Gly Tyr Leu Val Cys Ser Gly Ile
        995                 1000                1005

Pro Lys Arg Asn Gly Asp Gln His Ala Lys Glu Ile Ala Glu Leu Ser
   1010                1015                1020

Phe Ala Phe Leu Arg Thr Val Ser Ser Phe Arg Val Asp His Leu Pro
025                 1030                1035                1040

Ser Glu Arg Val Asn Leu Arg Ile Gly Phe His Ser Gly Pro Ala Val
               1045                1050                1055

Ala Gly Val Val Gly Leu Thr Met Pro Arg Tyr Cys Leu Phe Gly Asp
           1060                1065                1070

Ser Val Asn Thr Ala Ser Arg Met Glu Ser Asn Gly Lys Ala Gly Arg
       1075                1080                1085

Val His Ile Ser Ser Ser Ala Asn His Phe Leu Thr Ser Val Ile Gly
   1090                1095                1100

Gly Tyr Val Thr Glu Pro Arg Gly Glu Val Ile Ile Lys Gly Lys Gly
105                 1110                1115                1120

Val Met Glu Thr Phe Trp Leu Leu Gly Arg Ile Gly Glu Ala His Leu
               1125                1130                1135

Ser Glu Gly Thr Ala Glu Arg Asn Ala Ser Ala Ala Thr Arg Lys
           1140                1145                1150


<210> SEQ ID NO 3
<211> LENGTH: 7127
<212> TYPE: DNA
<213> ORGANISM: Heterodera glycines

<400> SEQUENCE: 3

gaatggcgaa cagtcatttg ccgatattta tatgccaatc tccacctcta agccgaccga     60

actcatccgc cggttcttgg ctcactttgc cctttcattt ggctatattt catttccata    120

gctttaaatt tattcagacg tcaattgttg aattcgtttc gccattagct tttgtttatg    180

acttttccac atctgttcaa ataatttgaa caccaaaaac ttggcttttt tgattgctta    240

accattcatt ttgttaaatt tgccgttcat tttgtttgat cacctaaaaa atttggcgta    300

gtttttgtga tcacattagg agttgggacc aagttagcca atttttaggg gtgtattttt    360

cgttttttta aatcccgagc taggtggtgg attttccaaa atttttagcc gttttcattt    420

tttacttatt taatgggaaa atgtaaaacg gaaaaaatta aacgcatgga actgaaaaaa    480

ggaaatgaaa gatatttcaa acggaagagg aaaagaaaac tatcaaaaat taaagaaaat    540

tcttaagaaa aagcaccgat tatttatata tatattttta ttttttgctg aatatatttt    600

ttcattttta cttgtattat tataattttt tgtttattga taaggatttt aaaaatttcg    660

atatttctta gaattaaaat ttgtcactct gtcaggactt tgaactttaa aaaatttgaa    720

ctttggcggt aaaattattt aacgatgccc tcccaaacaa agctgaagag gaagtggatg    780

gaatcacttc aaaagaacga attcattttg gaattttgaa atgcccttta agggattatg    840

cgactgccgc aaaacgaccg taccgaatca gcttgaaaca ttttgtaagg tttctccgct    900

gggatttgaa tcccgacaaa tcgccttttt aatgaattca tttcatttta aaatttcctt    960

gcccaaaatc tctcaaaatg gaaatgccgt cctgtttctt cctccttttc tttcttatgc   1020

tttttgtcag cccttctcgg caccaattag tcactgttag caactcatcg tcttcgccca   1080

ttggcaccac cgtcgctttt ggcactcctt cgccgatcat cccaatctct actgcaccct   1140

ccacgaatgg cactgccact tttggcgtcc ctccgccgat cagtccgccg attaattctt   1200
```

-continued

```
cgtcctctct cccatcaact ggtcctttgg aagcatcggt tcagttaaaa atcggcttcc   1260
tctttgctaa cggcacccaa cggttgcgaa tgcttttcgg ctttggccaa tccgcgcccg   1320
ccgtcacttt ggcactcgaa cgggcgaggc aggagcacct catcgacagc atcaacttca   1380
cgtgggcaat tggaatgaat ttagaaactc acaattttca aatcactttt tgcaaattta   1440
aaaatctcca agcgagcgga aataattggc cgtaaatgcc aatttcagtt acacgtggcg   1500
aatgtgcggc tgctttcagc cttgggctgt cggctacgcc actcaactgg ttctgacgga   1560
aaatgtggac gctttgatcg gtccgccttg tgtgaccagt aatgcctttt tgtttgacac   1620
tttgccaaaa attgcgtaaa tgaaaaaggt gccatcgccg cgggatacgt ggcctccttc   1680
tacaacattc cactgtattt gtggggtgct actgtggcct cggaatttta caacactacc   1740
gtatacccta cactgaacaa cgtgaacgtt aactcggaca tgtcagtgga gaaaatattc   1800
ttcgccttcc atcccctaaa attattattt ctactaataa aataaactaa aatggatttg   1860
ctttacgagc cgtcaccaaa tcaaatgacc aatgatttct tattaatttc aacaattatt   1920
gcaggttggc gttggcctta caaagtgtgt tggtgcaatt caattggaca gaagtgtcct   1980
tcgtgtacac tccggacaat gagcgaatgt aagaattatt ttgaataatt aattaattaa   2040
ttagctatta atataattta attagggtct gtaactcggt gaaacagagt ctcacaaatg   2100
tgctcaacgt gaccaatgtg accattgttt tccagcatca gatggagtcc aatgtggaca   2160
gtatgaaggc gacgctgaga aatctgcgca accgatcgcg aagtgatggg ataattaatt   2220
tgatagcatc gctaattacc atcaattagt tgtgctttcc tgtttcgatg tcgaagttga   2280
acgtcgcaac tttctgttgt ccattttcga cactggtctt gctgcggaca acgaatttgt   2340
gttcatcatg ggatccctgc gcaaccaggg catgctccag cagggtaatt aggcaaatgg   2400
ccaaattagg ggagggataa ttaaaggggc aattgattag acctaacagt gcttcagttg   2460
cgtcgcgtga ggacggcagt gtcaaatatg tgaacaattg gatggacaaa aacagcccag   2520
gcgatggccg cgactcggac gcactcgccg cgacaaaaca cgtcataatg gtcaatccac   2580
ggcgaagcca agcaaattta agtgccttag tgtcgttcag attgacctgg aaaaccaatc   2640
gagtgatcag cttaacgaat tcaaccgaaa tttgagtgcg aaattcggca cttatccctt   2700
tttctgcaac ggaagttgca tgggcggcgc aacagaacaa tcggttgcaa tttgcacgaa   2760
aaatggaaat tataaaaaaa gataatgctt tttagccgtc gcaatacgcc agggctttgt   2820
tcgacacaac atacgcatat tttagagcat tgaatcgcac aatggaaaag cgcaaatcga   2880
atgggaggga ttgttgcgca acggcacgga attgaacgca gaaactgccg ggacgacctt   2940
tcagggtgag gtggagagga agaaaaggag gggggggggt agaagcgaat ttgggagagg   3000
aaccaatgga taaagcctgg caaaatgatg gagcattaag gcgagaccgg acgcatcact   3060
tttgacgccc acggcaaccg ccagccgacc ttttttgtga cgatgctaaa cgcactgaat   3120
gtgcccactg ttatggtgaa agtgaacatt accaacggag tattggtgcg aatggattaa   3180
gcggcggcgg attcttattt ttgaaattca acagaaaatg gaacggctgt acggcagtga   3240
ggcgtcgctg tgggtcaatt ggggcggctt tcggccgatg accacgccgt tgtgcggcta   3300
caacggcaca atgtgtggcc aaaatgtgac ggtgtacatt ctgatcggcg ttacgcttat   3360
gttgctgttg ctggtcgccg ctttgcttgg catcggatac gcaattcggt aaacagagga   3420
aaagcatcgg actgtgccga tcaaaaattg atttaaaagc aaagccaatg gtcgataatt   3480
ggaccaaaag gaatgttaac gccaaaatca ctcattaatt ataaatttta agcttttaat   3540
gcattaattg gaccgaattt ctccgaattg gcacaactta agcccattaa tccgccgatt   3600
```

-continued

```
ttgccatttg cagggagaaa atgcgcgaga agcagcgcct gacacgcgag tgtttgatcc   3660
catttgcaga gctgcgcaac ctgaaagagc tgcgcagttc ggaggaactg aagtcggaga   3720
cggagaagag catgcggagc atgcgtagca gtcagtcggg tgagcgtacg gtagcgacca   3780
ttcgctcaaa tatggcatat ggtaacgcag gaagcacacg gcttacggtc ggcagccaca   3840
aagcgcagcg ggagacggcc aattgcgcgt tctttgtgtt caaccgggaa attgtgctgg   3900
ccgtgaaata ccacgtcagg gtgcgaatta tgtccgaaga tttggccttc attaggaagg   3960
taaatgggac aacggcagga gaccatgttg gaaaatgtga ctaattacct aaagatgggt   4020
caatcgttac catataatat atacttccgt cgttacggta cagctgcggc agttggacca   4080
cgacaacatg aacaagttgt acggcgtgtg caccgatggg cccctttt gt tcgcaatttg   4140
gcgcaattgt cagcgaggga cattaaaagt gcaatttgac agaaaataac atttgttcag   4200
taaaataaca tgtcatgtca ttaaggaact gatcgccaag gagcaatacg ttggggacaa   4260
ttgtgtgatg tttgctctga tgcgggacat tgcaaatgta aacactcaca tgggaagtgc   4320
tttggcattg gcacttccca tcagctgttt ctttcctaaa tcggggccat tttcggggat   4380
ctccgacctc gacattcttc tgtcataatt ggcggcttgc cgtttccaat ttcttctgca   4440
taaattcgaa tttcggtcac tccatcccca gggtctgctc gccatccatc aatcgttcat   4500
cggagcccac gggctgctct cctctgaaaa ttgtctgatc aatgaccggt ggcaagtgaa   4560
aatcagcgac tttggcctga atatgatcag agaaagtcaa acgctgtcga agaaaggttg   4620
gcattgggtt tacgaagtaa ttcgcgtaat ttgcgccatt taaagcactt ttgtggacgg   4680
cgcctgaact tttgcgagaa aacaatcgga agggaacaaa agagggcgat gtgttcagtt   4740
ttgcgatcat ttgtgtggaa atggtgaaca gagagacggt gtggaacgga gtggaaaggg   4800
accaagacat cgatggtggg agggcggagg aggggatttg gaggggaaat ttcggcactc   4860
ggcttttcct tttccatcgg tgccattgtc cgacctttct ttagaaatcc tttatcggct   4920
cagacgcacc aacaccacaa tccctcaccg tccgcagctt catccccgcg cagagattaa   4980
ccaaagtttg gtatgcgcac gcatttctca tggcattttg ctgctgctat tctgtcttat   5040
accatatccc cacttaccgt aagcttcatc tgatcagaga ctgttggtcc gaagtgccgt   5100
ccgaacgtcc gcgcatggac attgtgcgaa cgatgctcaa acagatggtc caggacgggt   5160
cagtaagtca acagcggagc aatcaatgga cacgcttgtg atgctcgaaa gtctcgagag   5220
agcagtctcg gggtttttta atgcccttga ccgggtcaaa gcttgagtat cggcgatctt   5280
aagtagaaca agcgcttttc cgatccgctt ttgccccccc ccccaatttt tgcccatttc   5340
ctttctcttc agcagtcaaa atctgatgga ttacgtgttc ggcatgttgg agcagtacgc   5400
gagttcgctg gagcaggagg tggaggaacg gaccaaagag ttggtggagg agaagcgcaa   5460
gagcgacatt cttctctacc ggatgttgcc gcggcaggtg gcggacaaac tgaagatagg   5520
cgagtctgtg gagccagaat ccttccaaat ggccaccatt ttcttctccg acgtcgtctc   5580
cttcaccact ttggccggca aatgctcgcc attgcaagtg ccgtaaaaaa agaaaattta   5640
ccgctacact tttggaaaaa taaattgtcg catatttttc agaccccaat taatcaatta   5700
atttaaatca aacaagattg atcaaaatgg gaaatactga tcaattacat tgatcaaaat   5760
ggggaggaat cgactgatca atcccatccg tccccacccc tctcttctcg tttaggttgt   5820
gaatctgctc aacggtctgt acacagcctt tgacgggatc attgacactc atgactgcta   5880
caaagttggt aagtgaccag cgaatacctc actaatcgtc ttcaactctc tctcctccta   5940
```

-continued

```
ttttattgct ttgtattagt tctaatttgc cattttaatt gccccccgcc acttctcccc   6000

tcagaaacca ttggcgatgg ctatttggtc tgttcgggca ttccgaagcg caacggcgac   6060

caacacgcga aagaaatagc cgaactttcg ttcgccttcc ttcgcactgt gtccagcttc   6120

cgtgtcgatc acctcccctc cgaacgggtc aaccttcgca ttggcttcca ttccggttcg   6180

ttttcgctat taccgaatca aaaagactcc caacggcacc ccggggcatt ccctggcttc   6240

ttcccaattt ggcatttctt tacgaatgcc atggttaatt aattaattag gaccagcggt   6300

cgctggcgtc gtcggactga caatgccgcg ctattgtctc tttggggact cagtgaacac   6360

ggccagccga atggagtcaa acggaaaggg taaataaacg ggagaaaaag cgaaacaaaa   6420

caaatcaaat taatttggca accattttca gcaggccgag tgcacatttc atcaagtgcc   6480

aaccactttt tgaccagtgt aatcggcgga tatgtgacag agccaagagg cgaagtgatt   6540

ataaaggtca ttaattaagg atgggggcaa tggctccaat tagtcggtta atcccattat   6600

tagggcaaag gagtgatgga gaccttttgg ctgttagggc gaattggaga ggcacatttg   6660

tcggagggca cagcggaaag aaatgcgagt gccgcaacga gaaaatgaag aaacatcaca   6720

cggcattccc tctgatcact cattttaatg actcgaaatc attgaccaat tttaatgaat   6780

tttaatctct tttattatta tgatagcgca atttttgcgc acatttaagc gataacaatt   6840

tttatattaa agttcccctt aacaaattta ctattgtaaa tactgtctcg aatacaaaaa   6900

atgtataatt tactattttt ctcacgatat tcatggcaaa aaggtcatcc ctaattatta   6960

aacgttactc tttcatgtgt tcattaacac acaataattt tttgtctcag atttactaat   7020

tacatataca ataagaacaa aaatattttt tggaaaaagt ttacaatata aagataatat   7080

taaaggagca attagtgaaa atgcatataa ttagaaatga tcgagtc                 7127


<210> SEQ ID NO 4
<211> LENGTH: 3499
<212> TYPE: DNA
<213> ORGANISM: Heterodera glycines
<220> FEATURE:
<221> NAME/KEY: CDS
<222> LOCATION: (3)..(3347)

<400> SEQUENCE: 4

at ttc gtt ccg atg ttt ttt ggg aca tcg gtt gct gtt gtt ctt tgt        47
   Phe Val Pro Met Phe Phe Gly Thr Ser Val Ala Val Val Leu Cys
     1               5                  10                  15

tgg ctt ttt tgc act ttc cca acg aca ttc ggc caa cag caa aat ggg       95
Trp Leu Phe Cys Thr Phe Pro Thr Thr Phe Gly Gln Gln Gln Asn Gly
                20                  25                  30

act gcg ccg ctg atc aaa gtc ggg cta atg atg ccg cac aat cag tcg      143
Thr Ala Pro Leu Ile Lys Val Gly Leu Met Met Pro His Asn Gln Ser
            35                  40                  45

tcc gat ttg tct ttt gcc cga tcc gcc ggt gcc atc tca gtg gcg ctg      191
Ser Asp Leu Ser Phe Ala Arg Ser Ala Gly Ala Ile Ser Val Ala Leu
        50                  55                  60

aag cac att ttc aac gac aat ttg ttg cct ccc ggc acc aat ttc agt      239
Lys His Ile Phe Asn Asp Asn Leu Leu Pro Pro Gly Thr Asn Phe Ser
     65                  70                  75

ttc att gtc cgt ttc gaa gag tgc cta atg tcc gtc gcc gcc ggg tac      287
Phe Ile Val Arg Phe Glu Glu Cys Leu Met Ser Val Ala Ala Gly Tyr
 80                  85                  90                  95

gcc ttc gat ttg ttg gat ggc cag caa gtg gac ctt ttc att gcg ccg      335
Ala Phe Asp Leu Leu Asp Gly Gln Gln Val Asp Leu Phe Ile Ala Pro
                100                 105                 110
```

-continued

```
ccg tgc acc gac agt gcg caa gtt gca ctt ttc gtg tcc aca ttt tac      383
Pro Cys Thr Asp Ser Ala Gln Val Ala Leu Phe Val Ser Thr Phe Tyr
            115                 120                 125

aac atc cct tcc atc aca tgg ggc cag aat tcg gac tcc tct ttc aat      431
Asn Ile Pro Ser Ile Thr Trp Gly Gln Asn Ser Asp Ser Ser Phe Asn
        130                 135                 140

tcg cag agc aat tac ccc act ttg ctg agt gcg ctt ccc aat tac gcc      479
Ser Gln Ser Asn Tyr Pro Thr Leu Leu Ser Ala Leu Pro Asn Tyr Ala
    145                 150                 155

gac ttt ggc caa att atc att tcg ctg tgc atc ttc ttc aag tgg tcc      527
Asp Phe Gly Gln Ile Ile Ile Ser Leu Cys Ile Phe Phe Lys Trp Ser
160                 165                 170                 175

gtc atg gca ctg att tat cag ctc agc gag acg ggt caa tgc gcg tcg      575
Val Met Ala Leu Ile Tyr Gln Leu Ser Glu Thr Gly Gln Cys Ala Ser
                180                 185                 190

ttc cag caa gac ttg cag atc gcg atc aat tcc aac gac aaa tgc gat      623
Phe Gln Gln Asp Leu Gln Ile Ala Ile Asn Ser Asn Asp Lys Cys Asp
            195                 200                 205

atc agc tac aga gag gaa gtt aag atc agt tct gcg ggc acc agc gac      671
Ile Ser Tyr Arg Glu Glu Val Lys Ile Ser Ser Ala Gly Thr Ser Asp
        210                 215                 220

gcc caa tac acc ata agt caa att cag agc agg gcg aga atc gtc att      719
Ala Gln Tyr Thr Ile Ser Gln Ile Gln Ser Arg Ala Arg Ile Val Ile
    225                 230                 235

ctt tgc ttc gac gag ttt gtt cag ctg cgc aac ttt gcc gcc aaa ctt      767
Leu Cys Phe Asp Glu Phe Val Gln Leu Arg Asn Phe Ala Ala Lys Leu
240                 245                 250                 255

cag gag ggt ggc ttg gac tcc gct gac tac gtt tat ctc atc ccc gga      815
Gln Glu Gly Gly Leu Asp Ser Ala Asp Tyr Val Tyr Leu Ile Pro Gly
                260                 265                 270

ctc acc atg gat gat agt att gaa agt gtt aat tgt gtc ttt tat aaa      863
Leu Thr Met Asp Asp Ser Ile Glu Ser Val Asn Cys Val Phe Tyr Lys
            275                 280                 285

att caa att tgc gtt tgc ttt ttc tct gtt ttt aat tta ctt ttt gtt      911
Ile Gln Ile Cys Val Cys Phe Phe Ser Val Phe Asn Leu Leu Phe Val
        290                 295                 300

ttg ggt ggc tcc aag gcc acc gcg tgg tgg gtc gac ccg aac ccg acc      959
Leu Gly Gly Ser Lys Ala Thr Ala Trp Trp Val Asp Pro Asn Pro Thr
    305                 310                 315

atc caa tca gcg gcc tac aga att gct cag cgc agt ctt tat ctg atg     1007
Ile Gln Ser Ala Ala Tyr Arg Ile Ala Gln Arg Ser Leu Tyr Leu Met
320                 325                 330                 335

ttg gac atc ttc aac aaa gtc gca act tca ggt caa gtg ggc aac ggc     1055
Leu Asp Ile Phe Asn Lys Val Ala Thr Ser Gly Gln Val Gly Asn Gly
                340                 345                 350

act tcg ttt gat cag gaa gtg atc aga cag gtc acc caa tgg ccc ttc     1103
Thr Ser Phe Asp Gln Glu Val Ile Arg Gln Val Thr Gln Trp Pro Phe
            355                 360                 365

ttc tgt acc gat tgc gat cag tcg ttg cag gct tct tct tac gcc cct     1151
Phe Cys Thr Asp Cys Asp Gln Ser Leu Gln Ala Ser Ser Tyr Ala Pro
        370                 375                 380

ttg ctc cac gac agt ttc tat ttg tat gcc atg gcc ctt tcc aaa gcg     1199
Leu Leu His Asp Ser Phe Tyr Leu Tyr Ala Met Ala Leu Ser Lys Ala
    385                 390                 395

gca aaa att gcc ggc gca ttg tca cct tcc gtt tac cga aat ggc caa     1247
Ala Lys Ile Ala Gly Ala Leu Ser Pro Ser Val Tyr Arg Asn Gly Gln
400                 405                 410                 415

ttg att cgc tcc caa acc gcc aat ttg tct ttt gaa gga atg acg ggg     1295
Leu Ile Arg Ser Gln Thr Ala Asn Leu Ser Phe Glu Gly Met Thr Gly
                420                 425                 430
```

-continued

```
tca aac aaa ttt gga tct gat gga ctt cgt aat ttc att tac ctt gtc     1343
Ser Asn Lys Phe Gly Ser Asp Gly Leu Arg Asn Phe Ile Tyr Leu Val
            435                 440                 445

tcc atg tat tcg agc ttg aac ggt gac ttg act tcg tat gtg tgg ctc     1391
Ser Met Tyr Ser Ser Leu Asn Gly Asp Leu Thr Ser Tyr Val Trp Leu
        450                 455                 460

caa atg aac gat gcc gga gtg aat tct tca tgg att aat gcc acg gcc     1439
Gln Met Asn Asp Ala Gly Val Asn Ser Ser Trp Ile Asn Ala Thr Ala
    465                 470                 475

gag aag ctg att tgg tcg agc cga aac ggc gtt aag cca ttg gcc gtg     1487
Glu Lys Leu Ile Trp Ser Ser Arg Asn Gly Val Lys Pro Leu Ala Val
480                 485                 490                 495

ccg ttg tgc gga ttt gac ggc aac ggc tgt cac atg gac ttc ttc acg     1535
Pro Leu Cys Gly Phe Asp Gly Asn Gly Cys His Met Asp Phe Phe Thr
                500                 505                 510

gag tac cgt ggg tat gtg ata gct gcc ggc tgt ctg ttg ctg ctc att     1583
Glu Tyr Arg Gly Tyr Val Ile Ala Ala Gly Cys Leu Leu Leu Leu Ile
            515                 520                 525

ttg ggc tcg ttc gcc ttc ggc att tac tgg ctg ttc caa tcc aag gcg     1631
Leu Gly Ser Phe Ala Phe Gly Ile Tyr Trp Leu Phe Gln Ser Lys Ala
        530                 535                 540

cgc gag atg gaa cgg caa aat cgc ctc tgg caa atc gcc tac agt act     1679
Arg Glu Met Glu Arg Gln Asn Arg Leu Trp Gln Ile Ala Tyr Ser Thr
    545                 550                 555

ctg acg ccg gcg ggc acc aaa aag aaa atg atg gaa agt gtg cgc tct     1727
Leu Thr Pro Ala Gly Thr Lys Lys Lys Met Met Glu Ser Val Arg Ser
560                 565                 570                 575

ctc cag tcg agc act tct tct cag ttc acg cgc gac tcc tcc cat tcc     1775
Leu Gln Ser Ser Thr Ser Ser Gln Phe Thr Arg Asp Ser Ser His Ser
                580                 585                 590

cac gtt tcc atc aaa cac aac ttc aat ggc atc gtg tac att atg aac     1823
His Val Ser Ile Lys His Asn Phe Asn Gly Ile Val Tyr Ile Met Asn
            595                 600                 605

ggc gag cgg gtg atc ggc att cag cat tcg gtt ggc att cga ctc agt     1871
Gly Glu Arg Val Ile Gly Ile Gln His Ser Val Gly Ile Arg Leu Ser
        610                 615                 620

cca cag gac atg gcc gag ctg aga act atg cgc ctt ttg gat gga gac     1919
Pro Gln Asp Met Ala Glu Leu Arg Thr Met Arg Leu Leu Asp Gly Asp
    625                 630                 635

aat gtg aac cga ttc atc ggc ctt tcc atc gat ggc gcc gcg ctt ctc     1967
Asn Val Asn Arg Phe Ile Gly Leu Ser Ile Asp Gly Ala Ala Leu Leu
640                 645                 650                 655

tcc ctg tgg cgc tac tgc tcg cgt ggc ccc ctt tcg gac gtg atc tcg     2015
Ser Leu Trp Arg Tyr Cys Ser Arg Gly Pro Leu Ser Asp Val Ile Ser
                660                 665                 670

ggc tct tcc tct ctg acc atg gac ggc ttc ttc att tat tcg ttg gtc     2063
Gly Ser Ser Ser Leu Thr Met Asp Gly Phe Phe Ile Tyr Ser Leu Val
            675                 680                 685

cgc gac gtt gcc gaa gga ttg cgc ttc ctt cac gcg tcc tca att gga     2111
Arg Asp Val Ala Glu Gly Leu Arg Phe Leu His Ala Ser Ser Ile Gly
        690                 695                 700

tgg tat ggc aat ttg cgt tcc acc aac tgt ttg atc gac gac cgt tgg     2159
Trp Tyr Gly Asn Leu Arg Ser Thr Asn Cys Leu Ile Asp Asp Arg Trp
    705                 710                 715

caa ata aaa ctg tcc gag ttt ggt ctc cgc ttc ttt cgt gca cac gaa     2207
Gln Ile Lys Leu Ser Glu Phe Gly Leu Arg Phe Phe Arg Ala His Glu
720                 725                 730                 735

aaa cgg gag gca aaa gat ttg gtt tgg aca gcg cca gaa ttg ttg cgc     2255
Lys Arg Glu Ala Lys Asp Leu Val Trp Thr Ala Pro Glu Leu Leu Arg
```

-continued

```
                740                 745                 750

gat aat gac atc gtt ggc aac aaa ttt ggc gat gtt tac agc ttt tcc     2303
Asp Asn Asp Ile Val Gly Asn Lys Phe Gly Asp Val Tyr Ser Phe Ser
            755                 760                 765

atc gtt tct tcc gaa att gtg aat atg aag cca att tgg gag cag gac     2351
Ile Val Ser Ser Glu Ile Val Asn Met Lys Pro Ile Trp Glu Gln Asp
        770                 775                 780

gaa gcg aag gga aat gtt gaa agg gtc cga acc ggg ggg aag agg gca     2399
Glu Ala Lys Gly Asn Val Glu Arg Val Arg Thr Gly Gly Lys Arg Ala
    785                 790                 795

ttt cgt ccc aaa ttg gag ccg agc agc cag gac ttg tcc ccg gca ctg     2447
Phe Arg Pro Lys Leu Glu Pro Ser Ser Gln Asp Leu Ser Pro Ala Leu
800                 805                 810                 815

ctg cat ctg atc aaa gac tgc tgg gac gaa agc cct gca gaa cgg cca     2495
Leu His Leu Ile Lys Asp Cys Trp Asp Glu Ser Pro Ala Glu Arg Pro
                820                 825                 830

aaa atg gag acg gtg acc gca ctt ttg cag tca atg aac acg gga agg     2543
Lys Met Glu Thr Val Thr Ala Leu Leu Gln Ser Met Asn Thr Gly Arg
            835                 840                 845

agc acc aat ttg atg gac cac gtg ttc aat atg ctg gaa gtg tac gcc     2591
Ser Thr Asn Leu Met Asp His Val Phe Asn Met Leu Glu Val Tyr Ala
        850                 855                 860

ggc tca ttg gag gag gaa gtt gag gaa cgg acc aaa gag ttg gtg gag     2639
Gly Ser Leu Glu Glu Glu Val Glu Glu Arg Thr Lys Glu Leu Val Glu
    865                 870                 875

gag aag aag aag acg gac atc ctt ctc tac cga atg ctg ccc aaa caa     2687
Glu Lys Lys Lys Thr Asp Ile Leu Leu Tyr Arg Met Leu Pro Lys Gln
880                 885                 890                 895

gtc gcc gac aaa ctc aaa ttg ggc caa tct gtg gag ccc gaa acc ttc     2735
Val Ala Asp Lys Leu Lys Leu Gly Gln Ser Val Glu Pro Glu Thr Phe
                900                 905                 910

gac tgc gtt acc gta ttc ttc tcg gac gtc gtc tca ttc aca aca atc     2783
Asp Cys Val Thr Val Phe Phe Ser Asp Val Val Ser Phe Thr Thr Ile
            915                 920                 925

gct tca aaa tgc tca cct ttg cag gtg gtc aat ttg ctg aac aat ctg     2831
Ala Ser Lys Cys Ser Pro Leu Gln Val Val Asn Leu Leu Asn Asn Leu
        930                 935                 940

tac act ctg ttg gac tca atc atc gcc gaa ttt gac gtg tac aaa gtt     2879
Tyr Thr Leu Leu Asp Ser Ile Ile Ala Glu Phe Asp Val Tyr Lys Val
    945                 950                 955

gag aca att ggc gat ggt tat ttg tgc gtg tcg ggc ctt ccc cac cgc     2927
Glu Thr Ile Gly Asp Gly Tyr Leu Cys Val Ser Gly Leu Pro His Arg
960                 965                 970                 975

aat ggg cat gaa cac gcg caa cac atc gcc aaa atg tcg ttg gca ttc     2975
Asn Gly His Glu His Ala Gln His Ile Ala Lys Met Ser Leu Ala Phe
                980                 985                 990

atg cgc aac ttg ggc agc ttc acc att ccc cac ttg ccc att gaa cgg     3023
Met Arg Asn Leu Gly Ser Phe Thr Ile Pro His Leu Pro Ile Glu Arg
            995                1000                1005

ctt cgt ctc cgc att ggc att cac acc ggc tcc acc gtg gcg ggc gtt     3071
Leu Arg Leu Arg Ile Gly Ile His Thr Gly Ser Thr Val Ala Gly Val
       1010                1015                1020

gtc ggt ctt tcc atg ccc cgt tat tgt ctg ttc ggc gac aca att aac     3119
Val Gly Leu Ser Met Pro Arg Tyr Cys Leu Phe Gly Asp Thr Ile Asn
   1025                1030                1035

aca gcg gca cgg ctg gaa agc agc tca aag ccg atg cga att cac att     3167
Thr Ala Ala Arg Leu Glu Ser Ser Ser Lys Pro Met Arg Ile His Ile
1040                1045                1050                1055

tcc acg acg acg aat cac ttt ttg gtc aat gtt ctc gga ggt ttt gtc     3215
```

-continued

```
Ser Thr Thr Thr Asn His Phe Leu Val Asn Val Leu Gly Gly Phe Val
              1060                1065                1070

acc caa gcg cgt gga gaa att tta gtg aag gga aag ggc gtt ctc gaa     3263
Thr Gln Ala Arg Gly Glu Ile Leu Val Lys Gly Lys Gly Val Leu Glu
          1075                1080                1085

acc ttt tgg ctg ctt ggc ctc gaa ggc gac ccg gcg gtg atg cga atg     3311
Thr Phe Trp Leu Leu Gly Leu Glu Gly Asp Pro Ala Val Met Arg Met
      1090                1095                1100

ttg cac agt tcg gac ggt aat aat gcg act acg gaa tgaacaaaaa          3357
Leu His Ser Ser Asp Gly Asn Asn Ala Thr Thr Glu
   1105                1110                1115

caaattgagg aagaaattga acacaaagga aacagaaaaa ccaaaagaat gaatgaatga   3417

atgatttgtc atttgtaaaa attaaaatgt cggacaacaa aaaaaatcga aaggaacgaa   3477

aaaaaaaaaa aaaaaaaaaa aa                                            3499


<210> SEQ ID NO 5
<211> LENGTH: 1115
<212> TYPE: PRT
<213> ORGANISM: Heterodera glycines

<400> SEQUENCE: 5

Phe Val Pro Met Phe Phe Gly Thr Ser Val Ala Val Val Leu Cys Trp
  1               5                  10                  15

Leu Phe Cys Thr Phe Pro Thr Thr Phe Gly Gln Gln Gln Asn Gly Thr
             20                  25                  30

Ala Pro Leu Ile Lys Val Gly Leu Met Met Pro His Asn Gln Ser Ser
        35                  40                  45

Asp Leu Ser Phe Ala Arg Ser Ala Gly Ala Ile Ser Val Ala Leu Lys
    50                  55                  60

His Ile Phe Asn Asp Asn Leu Leu Pro Pro Gly Thr Asn Phe Ser Phe
 65                  70                  75                  80

Ile Val Arg Phe Glu Glu Cys Leu Met Ser Val Ala Ala Gly Tyr Ala
                 85                  90                  95

Phe Asp Leu Leu Asp Gly Gln Gln Val Asp Leu Phe Ile Ala Pro Pro
            100                 105                 110

Cys Thr Asp Ser Ala Gln Val Ala Leu Phe Val Ser Thr Phe Tyr Asn
        115                 120                 125

Ile Pro Ser Ile Thr Trp Gly Gln Asn Ser Asp Ser Ser Phe Asn Ser
    130                 135                 140

Gln Ser Asn Tyr Pro Thr Leu Leu Ser Ala Leu Pro Asn Tyr Ala Asp
145                 150                 155                 160

Phe Gly Gln Ile Ile Ile Ser Leu Cys Ile Phe Phe Lys Trp Ser Val
                165                 170                 175

Met Ala Leu Ile Tyr Gln Leu Ser Glu Thr Gly Gln Cys Ala Ser Phe
            180                 185                 190

Gln Gln Asp Leu Gln Ile Ala Ile Asn Ser Asn Asp Lys Cys Asp Ile
        195                 200                 205

Ser Tyr Arg Glu Glu Val Lys Ile Ser Ser Ala Gly Thr Ser Asp Ala
    210                 215                 220

Gln Tyr Thr Ile Ser Gln Ile Gln Ser Arg Ala Arg Ile Val Ile Leu
225                 230                 235                 240

Cys Phe Asp Glu Phe Val Gln Leu Arg Asn Phe Ala Ala Lys Leu Gln
                245                 250                 255

Glu Gly Gly Leu Asp Ser Ala Asp Tyr Val Tyr Leu Ile Pro Gly Leu
            260                 265                 270
```

-continued

```
Thr Met Asp Asp Ser Ile Glu Ser Val Asn Cys Val Phe Tyr Lys Ile
        275                 280                 285

Gln Ile Cys Val Cys Phe Phe Ser Val Phe Asn Leu Leu Phe Val Leu
    290                 295                 300

Gly Gly Ser Lys Ala Thr Ala Trp Trp Val Asp Pro Asn Pro Thr Ile
305                 310                 315                 320

Gln Ser Ala Ala Tyr Arg Ile Ala Gln Arg Ser Leu Tyr Leu Met Leu
                325                 330                 335

Asp Ile Phe Asn Lys Val Ala Thr Ser Gly Gln Val Gly Asn Gly Thr
            340                 345                 350

Ser Phe Asp Gln Glu Val Ile Arg Gln Val Thr Gln Trp Pro Phe Phe
        355                 360                 365

Cys Thr Asp Cys Asp Gln Ser Leu Gln Ala Ser Ser Tyr Ala Pro Leu
    370                 375                 380

Leu His Asp Ser Phe Tyr Leu Tyr Ala Met Ala Leu Ser Lys Ala Ala
385                 390                 395                 400

Lys Ile Ala Gly Ala Leu Ser Pro Ser Val Tyr Arg Asn Gly Gln Leu
                405                 410                 415

Ile Arg Ser Gln Thr Ala Asn Leu Ser Phe Glu Gly Met Thr Gly Ser
            420                 425                 430

Asn Lys Phe Gly Ser Asp Gly Leu Arg Asn Phe Ile Tyr Leu Val Ser
        435                 440                 445

Met Tyr Ser Ser Leu Asn Gly Asp Leu Thr Ser Tyr Val Trp Leu Gln
    450                 455                 460

Met Asn Asp Ala Gly Val Asn Ser Ser Trp Ile Asn Ala Thr Ala Glu
465                 470                 475                 480

Lys Leu Ile Trp Ser Ser Arg Asn Gly Val Lys Pro Leu Ala Val Pro
                485                 490                 495

Leu Cys Gly Phe Asp Gly Asn Gly Cys His Met Asp Phe Phe Thr Glu
            500                 505                 510

Tyr Arg Gly Tyr Val Ile Ala Ala Gly Cys Leu Leu Leu Leu Ile Leu
        515                 520                 525

Gly Ser Phe Ala Phe Gly Ile Tyr Trp Leu Phe Gln Ser Lys Ala Arg
    530                 535                 540

Glu Met Glu Arg Gln Asn Arg Leu Trp Gln Ile Ala Tyr Ser Thr Leu
545                 550                 555                 560

Thr Pro Ala Gly Thr Lys Lys Lys Met Met Glu Ser Val Arg Ser Leu
                565                 570                 575

Gln Ser Ser Thr Ser Ser Gln Phe Thr Arg Asp Ser Ser His Ser His
            580                 585                 590

Val Ser Ile Lys His Asn Phe Asn Gly Ile Val Tyr Ile Met Asn Gly
        595                 600                 605

Glu Arg Val Ile Gly Ile Gln His Ser Val Gly Ile Arg Leu Ser Pro
    610                 615                 620

Gln Asp Met Ala Glu Leu Arg Thr Met Arg Leu Leu Asp Gly Asp Asn
625                 630                 635                 640

Val Asn Arg Phe Ile Gly Leu Ser Ile Asp Gly Ala Ala Leu Leu Ser
                645                 650                 655

Leu Trp Arg Tyr Cys Ser Arg Gly Pro Leu Ser Asp Val Ile Ser Gly
            660                 665                 670

Ser Ser Ser Leu Thr Met Asp Gly Phe Phe Ile Tyr Ser Leu Val Arg
        675                 680                 685
```

-continued

```
Asp Val Ala Glu Gly Leu Arg Phe Leu His Ala Ser Ser Ile Gly Trp
    690                 695                 700

Tyr Gly Asn Leu Arg Ser Thr Asn Cys Leu Ile Asp Asp Arg Trp Gln
705                 710                 715                 720

Ile Lys Leu Ser Glu Phe Gly Leu Arg Phe Phe Arg Ala His Glu Lys
                725                 730                 735

Arg Glu Ala Lys Asp Leu Val Trp Thr Ala Pro Glu Leu Leu Arg Asp
            740                 745                 750

Asn Asp Ile Val Gly Asn Lys Phe Gly Asp Val Tyr Ser Phe Ser Ile
        755                 760                 765

Val Ser Ser Glu Ile Val Asn Met Lys Pro Ile Trp Glu Gln Asp Glu
    770                 775                 780

Ala Lys Gly Asn Val Glu Arg Val Arg Thr Gly Gly Lys Arg Ala Phe
785                 790                 795                 800

Arg Pro Lys Leu Glu Pro Ser Ser Gln Asp Leu Ser Pro Ala Leu Leu
                805                 810                 815

His Leu Ile Lys Asp Cys Trp Asp Glu Ser Pro Ala Glu Arg Pro Lys
            820                 825                 830

Met Glu Thr Val Thr Ala Leu Leu Gln Ser Met Asn Thr Gly Arg Ser
        835                 840                 845

Thr Asn Leu Met Asp His Val Phe Asn Met Leu Glu Val Tyr Ala Gly
    850                 855                 860

Ser Leu Glu Glu Glu Val Glu Glu Arg Thr Lys Glu Leu Val Glu Glu
865                 870                 875                 880

Lys Lys Lys Thr Asp Ile Leu Leu Tyr Arg Met Leu Pro Lys Gln Val
                885                 890                 895

Ala Asp Lys Leu Lys Leu Gly Gln Ser Val Glu Pro Glu Thr Phe Asp
            900                 905                 910

Cys Val Thr Val Phe Phe Ser Asp Val Val Ser Phe Thr Thr Ile Ala
        915                 920                 925

Ser Lys Cys Ser Pro Leu Gln Val Val Asn Leu Leu Asn Asn Leu Tyr
    930                 935                 940

Thr Leu Leu Asp Ser Ile Ile Ala Glu Phe Asp Val Tyr Lys Val Glu
945                 950                 955                 960

Thr Ile Gly Asp Gly Tyr Leu Cys Val Ser Gly Leu Pro His Arg Asn
                965                 970                 975

Gly His Glu His Ala Gln His Ile Ala Lys Met Ser Leu Ala Phe Met
            980                 985                 990

Arg Asn Leu Gly Ser Phe Thr Ile Pro His Leu Pro Ile Glu Arg Leu
        995                 1000                1005

Arg Leu Arg Ile Gly Ile His Thr Gly Ser Thr Val Ala Gly Val Val
   1010                1015                1020

Gly Leu Ser Met Pro Arg Tyr Cys Leu Phe Gly Asp Thr Ile Asn Thr
025                1030                1035                104

Ala Ala Arg Leu Glu Ser Ser Ser Lys Pro Met Arg Ile His Ile Ser
               1045                1050                1055

Thr Thr Thr Asn His Phe Leu Val Asn Val Leu Gly Gly Phe Val Thr
           1060                1065                1070

Gln Ala Arg Gly Glu Ile Leu Val Lys Gly Lys Gly Val Leu Glu Thr
       1075                1080                1085

Phe Trp Leu Leu Gly Leu Glu Gly Asp Pro Ala Val Met Arg Met Leu
   1090                1095                1100

His Ser Ser Asp Gly Asn Asn Ala Thr Thr Glu
```

-continued

```
105                 1110                1115


<210> SEQ ID NO 6
<211> LENGTH: 3008
<212> TYPE: DNA
<213> ORGANISM: Heterodera glycines
<220> FEATURE:
<221> NAME/KEY: CDS
<222> LOCATION: (3)..(2849)

<400> SEQUENCE: 6

cg aaa atc aca att aat tat aaa aca cgc att ttc aac att caa tca        47
   Lys Ile Thr Ile Asn Tyr Lys Thr Arg Ile Phe Asn Ile Gln Ser
     1               5                  10                  15

tcc gac aca agc aca att gtc aat gca att cga gaa cgg gcg agg atc       95
Ser Asp Thr Ser Thr Ile Val Asn Ala Ile Arg Glu Arg Ala Arg Ile
                 20                  25                  30

gtt ttg ctt tgc ttt gac gat ttg aag cag atg cga act ttc gca ctt      143
Val Leu Leu Cys Phe Asp Asp Leu Lys Gln Met Arg Thr Phe Ala Leu
             35                  40                  45

caa ttg ttc gat gga gga cta aac aca aaa gat tat gtt tac ata atg      191
Gln Leu Phe Asp Gly Gly Leu Asn Thr Lys Asp Tyr Val Tyr Ile Met
         50                  55                  60

gtg gat aat gac atg tat tta tct ttc aat ttg acg aga tta cct ttt      239
Val Asp Asn Asp Met Tyr Leu Ser Phe Asn Leu Thr Arg Leu Pro Phe
     65                  70                  75

tgg gta caa tcg agt aac aat tca aat acg ctc gac gga aga aac gcg      287
Trp Val Gln Ser Ser Asn Asn Ser Asn Thr Leu Asp Gly Arg Asn Ala
 80                  85                  90                  95

gac gcc gaa gtg att ggc cga ttg gcc tta tgg tgg cac tac gac atc      335
Asp Ala Glu Val Ile Gly Arg Leu Ala Leu Trp Trp His Tyr Asp Ile
                100                 105                 110

act ttg tcc gcg ttg tcc aat caa aat tac tac ggc ttt ttc aaa aga      383
Thr Leu Ser Ala Leu Ser Asn Gln Asn Tyr Tyr Gly Phe Phe Lys Arg
            115                 120                 125

gtg atc gac aga acg ggc gat tgg ccc ttt tat tgc gat gaa tcc aat      431
Val Ile Asp Arg Thr Gly Asp Trp Pro Phe Tyr Cys Asp Glu Ser Asn
        130                 135                 140

tgc agc aaa gtg atc aat gca tcc atc tat tcg ctt ctg ttg tac gac      479
Cys Ser Lys Val Ile Asn Ala Ser Ile Tyr Ser Leu Leu Leu Tyr Asp
    145                 150                 155

gca att tac aat tac gga atg gca ctg aac gaa tct ttc cgc caa ttt      527
Ala Ile Tyr Asn Tyr Gly Met Ala Leu Asn Glu Ser Phe Arg Gln Phe
160                 165                 170                 175

ggc att cgg ccc gaa gtg tac cga aac ggc act ctg ttg gca cgg aac      575
Gly Ile Arg Pro Glu Val Tyr Arg Asn Gly Thr Leu Leu Ala Arg Asn
                180                 185                 190

aac aga aag cca ttc atg ggt ttg acc ggc tat gtg acg gtg gaa act      623
Asn Arg Lys Pro Phe Met Gly Leu Thr Gly Tyr Val Thr Val Glu Thr
            195                 200                 205

gat cag aac acg cgg gtg ttc gtt ttg tcc aat cgg aag tcg agc gag      671
Asp Gln Asn Thr Arg Val Phe Val Leu Ser Asn Arg Lys Ser Ser Glu
        210                 215                 220

aaa gga aat gcg cta cgc att tta atg caa ttc gca tgg gtc gag ggg      719
Lys Gly Asn Ala Leu Arg Ile Leu Met Gln Phe Ala Trp Val Glu Gly
    225                 230                 235

aaa ttg caa ata tcg ttg cga aat ggc agc ttg tcc atg tgg tcc tcc      767
Lys Leu Gln Ile Ser Leu Arg Asn Gly Ser Leu Ser Met Trp Ser Ser
240                 245                 250                 255

cgc ggt gga agc att cct ccg gcg gtg cca atc tgc ggc ttc gac ggc      815
Arg Gly Gly Ser Ile Pro Pro Ala Val Pro Ile Cys Gly Phe Asp Gly
```

-continued

```
            260                 265                 270

aaa ggg tgt gcc gcg tcg gtg ttc gaa atg tat aaa ggc tat tta ttg      863
Lys Gly Cys Ala Ala Ser Val Phe Glu Met Tyr Lys Gly Tyr Leu Leu
        275                 280                 285

ctt gga att gct ctt ttt gta gtg aca ata agc ggt agc act ttt act      911
Leu Gly Ile Ala Leu Phe Val Val Thr Ile Ser Gly Ser Thr Phe Thr
    290                 295                 300

gtc ggc ttt ttg ata cac gct aaa ttt gtg gaa ggt cgg aga agc aac      959
Val Gly Phe Leu Ile His Ala Lys Phe Val Glu Gly Arg Arg Ser Asn
305                 310                 315

atg agt tgg aaa ata cca ttt gct ttg ctg acg aaa tcg aaa cca aaa     1007
Met Ser Trp Lys Ile Pro Phe Ala Leu Leu Thr Lys Ser Lys Pro Lys
320                 325                 330                 335

cgt gcc gac cgc aca gcc gcc aac cga agt cgg cac tcc gtc cgc tcc     1055
Arg Ala Asp Arg Thr Ala Ala Asn Arg Ser Arg His Ser Val Arg Ser
                340                 345                 350

aac caa acg aac att tcc tcg ctg acc cat tcg acc att ggc agt ttg     1103
Asn Gln Thr Asn Ile Ser Ser Leu Thr His Ser Thr Ile Gly Ser Leu
            355                 360                 365

gca cgg tcc cga atc ttc tcc ctg tac tca tac aat ggg gaa aag tgc     1151
Ala Arg Ser Arg Ile Phe Ser Leu Tyr Ser Tyr Asn Gly Glu Lys Cys
        370                 375                 380

att gtg cgc agc ttt ggc tcc aca aca atg gca aag gca ttt aca gtg     1199
Ile Val Arg Ser Phe Gly Ser Thr Thr Met Ala Lys Ala Phe Thr Val
    385                 390                 395

aca caa atg gcc gag tgc cga acg atg cgt ctg ttc gac cat gag aat     1247
Thr Gln Met Ala Glu Cys Arg Thr Met Arg Leu Phe Asp His Glu Asn
400                 405                 410                 415

gtg aac cgg ttt ttg ggg ctg agt ttg gac ggg gcc aat gtg ttg gcc     1295
Val Asn Arg Phe Leu Gly Leu Ser Leu Asp Gly Ala Asn Val Leu Ala
                420                 425                 430

gtg tgg aac ttt tgc atg cgc ggg tcc atc aga gac gtg att ttg tct     1343
Val Trp Asn Phe Cys Met Arg Gly Ser Ile Arg Asp Val Ile Leu Ser
            435                 440                 445

gaa aat gcc atg gtc aaa gat gtg ata ttc atc cag tcg gcc atc aaa     1391
Glu Asn Ala Met Val Lys Asp Val Ile Phe Ile Gln Ser Ala Ile Lys
        450                 455                 460

gag att tgt gaa ggc att cat ttc ctg cac aat tcg ccc ctc caa ttc     1439
Glu Ile Cys Glu Gly Ile His Phe Leu His Asn Ser Pro Leu Gln Phe
    465                 470                 475

cat ggc cga ctg aaa tcc tcc gct tgt ttg atc aat gac cgg tgg caa     1487
His Gly Arg Leu Lys Ser Ser Ala Cys Leu Ile Asn Asp Arg Trp Gln
480                 485                 490                 495

gtc aaa att tca tat ttt ggg ctt cga tgg cta aag tct tca caa aaa     1535
Val Lys Ile Ser Tyr Phe Gly Leu Arg Trp Leu Lys Ser Ser Gln Lys
                500                 505                 510

aat cgg gcg aaa gat ctt tta tgg cta tcg cct gaa caa tta cgg aaa     1583
Asn Arg Ala Lys Asp Leu Leu Trp Leu Ser Pro Glu Gln Leu Arg Lys
            515                 520                 525

atg gga gac agc gaa att gtg gag ggg tca aaa cat tct gac att tac     1631
Met Gly Asp Ser Glu Ile Val Glu Gly Ser Lys His Ser Asp Ile Tyr
        530                 535                 540

acg atg gca tta atc ttc acc gaa atg gtt aat atg tct ccg tgt tgg     1679
Thr Met Ala Leu Ile Phe Thr Glu Met Val Asn Met Ser Pro Cys Trp
    545                 550                 555

gac agc agc gaa gcg gac gga gca gag gct gac cgg gcc gag gat gga     1727
Asp Ser Ser Glu Ala Asp Gly Ala Glu Ala Asp Arg Ala Glu Asp Gly
560                 565                 570                 575

gaa gag caa aac gga acg gaa atg tcg cga aga aag caa acg gcg gaa     1775
```

-continued

```
Glu Glu Gln Asn Gly Thr Glu Met Ser Arg Arg Lys Gln Thr Ala Glu
            580                 585                 590

acg gag gga gaa acg gca cag cgg cgc ccg ggg cga cgc gcg agg gga      1823
Thr Glu Gly Glu Thr Ala Gln Arg Arg Pro Gly Arg Arg Ala Arg Gly
        595                 600                 605

cgc aac gcg gag gaa atc gct tat ttg gtg aag cgg ggc gga atc gtt      1871
Arg Asn Ala Glu Glu Ile Ala Tyr Leu Val Lys Arg Gly Gly Ile Val
    610                 615                 620

ccg ctg cgg ccg atc att cgg ccg gca ttt gac cat ctg aac acg gaa      1919
Pro Leu Arg Pro Ile Ile Arg Pro Ala Phe Asp His Leu Asn Thr Glu
625                 630                 635

gtg att cat ctg atc cgc gac tgt tgg gtc gaa acg ccg agc gaa cgg      1967
Val Ile His Leu Ile Arg Asp Cys Trp Val Glu Thr Pro Ser Glu Arg
640                 645                 650                 655

ccg acc att gaa aaa gtg cga cag aaa ttg cgg caa atg ggt gcc caa      2015
Pro Thr Ile Glu Lys Val Arg Gln Lys Leu Arg Gln Met Gly Ala Gln
            660                 665                 670

cgg agg gtc aat ttg atg gac cat gtg ttc gac atg ttg gag cag tac      2063
Arg Arg Val Asn Leu Met Asp His Val Phe Asp Met Leu Glu Gln Tyr
        675                 680                 685

gcc aac aaa ttg gag gag gaa gtg cag gag cgg acc aaa gag ttg gag      2111
Ala Asn Lys Leu Glu Glu Glu Val Gln Glu Arg Thr Lys Glu Leu Glu
    690                 695                 700

ggg gag aag cga aag tcg gac att ctt ctc tat cgg atg atg cca cgc      2159
Gly Glu Lys Arg Lys Ser Asp Ile Leu Leu Tyr Arg Met Met Pro Arg
705                 710                 715

caa gtg gcg gac cga cta aag ctc ggc caa tcc gtg gag ccc gag cag      2207
Gln Val Ala Asp Arg Leu Lys Leu Gly Gln Ser Val Glu Pro Glu Gln
720                 725                 730                 735

ttc gac tgt gtg acg gtg ttc ttc tcg gac att gtc caa ttc gcg gca      2255
Phe Asp Cys Val Thr Val Phe Phe Ser Asp Ile Val Gln Phe Ala Ala
            740                 745                 750

ctg tcc aac caa atg cgg ccg ctg cag gtg gtc aat ctg atg aac gaa      2303
Leu Ser Asn Gln Met Arg Pro Leu Gln Val Val Asn Leu Met Asn Glu
        755                 760                 765

ctg tac acc atc ttc gac gca atc att gac gag cac gac gtg tac aag      2351
Leu Tyr Thr Ile Phe Asp Ala Ile Ile Asp Glu His Asp Val Tyr Lys
    770                 775                 780

ggc gat ggt tat ttg tgc gtg tct ggc ctt ccc aat cgg aat ggc act      2399
Gly Asp Gly Tyr Leu Cys Val Ser Gly Leu Pro Asn Arg Asn Gly Thr
785                 790                 795

ttg cat gcc aaa cac tgt gct gat atg gcg atc aaa ttt atg caa gcg      2447
Leu His Ala Lys His Cys Ala Asp Met Ala Ile Lys Phe Met Gln Ala
800                 805                 810                 815

ctg ctc aat ttc cga att ccc gac ctt cca aat gag cgc gtc cgt ctc      2495
Leu Leu Asn Phe Arg Ile Pro Asp Leu Pro Asn Glu Arg Val Arg Leu
            820                 825                 830

cga att ggg ctg cac agc ggc cca tgc gtc gcg gga gtc gtc ggg ttg      2543
Arg Ile Gly Leu His Ser Gly Pro Cys Val Ala Gly Val Val Gly Leu
        835                 840                 845

gcc atg ccc cgt tac tgt ttg ttt ggg gat acg gta aac acc gcc tcg      2591
Ala Met Pro Arg Tyr Cys Leu Phe Gly Asp Thr Val Asn Thr Ala Ser
    850                 855                 860

cgc atg gaa agt tct tca agc cca aac aaa att cac atg tcc agt gaa      2639
Arg Met Glu Ser Ser Ser Ser Pro Asn Lys Ile His Met Ser Ser Glu
865                 870                 875

acg ctc gaa ttg ctg cac aaa aat ttc aac ggc tct tat cac acg gag      2687
Thr Leu Glu Leu Leu His Lys Asn Phe Asn Gly Ser Tyr His Thr Glu
880                 885                 890                 895
```

-continued

```
agc aga ggc gaa gtg atc ata aag ggc aaa ggc gtc atg gag acc ttt     2735
Ser Arg Gly Glu Val Ile Ile Lys Gly Lys Gly Val Met Glu Thr Phe
                900                 905                 910

tgg ctg ttg ggc caa gtc gaa aat gga aca aca att aac gcc gat tat     2783
Trp Leu Leu Gly Gln Val Glu Asn Gly Thr Thr Ile Asn Ala Asp Tyr
            915                 920                 925

gcg cat aga atg cat ctg ccg gtg atc aaa ttt ggg gag gag gga aat     2831
Ala His Arg Met His Leu Pro Val Ile Lys Phe Gly Glu Glu Gly Asn
        930                 935                 940

gaa acc gga aaa aat gcg taaagaaatg gtgatgaagc caccacattt           2879
Glu Thr Gly Lys Asn Ala
    945

agactgaaat gcataatgaa agagcaaaga tcaagacttt caaaatgcct gaaattaatg   2939

taactttacc caaaatttag caaaaaattt caatttatta cgaaaaaaaa aaaaaaaaaa   2999

aaaaaaaaa                                                           3008


<210> SEQ ID NO 7
<211> LENGTH: 949
<212> TYPE: PRT
<213> ORGANISM: Heterodera glycines

<400> SEQUENCE: 7

Lys Ile Thr Ile Asn Tyr Lys Thr Arg Ile Phe Asn Ile Gln Ser Ser
  1               5                  10                  15

Asp Thr Ser Thr Ile Val Asn Ala Ile Arg Glu Arg Ala Arg Ile Val
            20                  25                  30

Leu Leu Cys Phe Asp Asp Leu Lys Gln Met Arg Thr Phe Ala Leu Gln
        35                  40                  45

Leu Phe Asp Gly Gly Leu Asn Thr Lys Asp Tyr Val Tyr Ile Met Val
     50                  55                  60

Asp Asn Asp Met Tyr Leu Ser Phe Asn Leu Thr Arg Leu Pro Phe Trp
 65                  70                  75                  80

Val Gln Ser Ser Asn Asn Ser Asn Thr Leu Asp Gly Arg Asn Ala Asp
                85                  90                  95

Ala Glu Val Ile Gly Arg Leu Ala Leu Trp Trp His Tyr Asp Ile Thr
            100                 105                 110

Leu Ser Ala Leu Ser Asn Gln Asn Tyr Tyr Gly Phe Phe Lys Arg Val
        115                 120                 125

Ile Asp Arg Thr Gly Asp Trp Pro Phe Tyr Cys Asp Glu Ser Asn Cys
    130                 135                 140

Ser Lys Val Ile Asn Ala Ser Ile Tyr Ser Leu Leu Leu Tyr Asp Ala
145                 150                 155                 160

Ile Tyr Asn Tyr Gly Met Ala Leu Asn Glu Ser Phe Arg Gln Phe Gly
                165                 170                 175

Ile Arg Pro Glu Val Tyr Arg Asn Gly Thr Leu Leu Ala Arg Asn Asn
            180                 185                 190

Arg Lys Pro Phe Met Gly Leu Thr Gly Tyr Val Thr Val Glu Thr Asp
        195                 200                 205

Gln Asn Thr Arg Val Phe Val Leu Ser Asn Arg Lys Ser Ser Glu Lys
    210                 215                 220

Gly Asn Ala Leu Arg Ile Leu Met Gln Phe Ala Trp Val Glu Gly Lys
225                 230                 235                 240

Leu Gln Ile Ser Leu Arg Asn Gly Ser Leu Ser Met Trp Ser Ser Arg
                245                 250                 255

Gly Gly Ser Ile Pro Pro Ala Val Pro Ile Cys Gly Phe Asp Gly Lys
```

-continued

```
            260                 265                 270

Gly Cys Ala Ala Ser Val Phe Glu Met Tyr Lys Gly Tyr Leu Leu Leu
        275                 280                 285

Gly Ile Ala Leu Phe Val Val Thr Ile Ser Gly Ser Thr Phe Thr Val
    290                 295                 300

Gly Phe Leu Ile His Ala Lys Phe Val Glu Gly Arg Arg Ser Asn Met
305                 310                 315                 320

Ser Trp Lys Ile Pro Phe Ala Leu Leu Thr Lys Ser Lys Pro Lys Arg
                325                 330                 335

Ala Asp Arg Thr Ala Ala Asn Arg Ser Arg His Ser Val Arg Ser Asn
            340                 345                 350

Gln Thr Asn Ile Ser Ser Leu Thr His Ser Thr Ile Gly Ser Leu Ala
        355                 360                 365

Arg Ser Arg Ile Phe Ser Leu Tyr Ser Tyr Asn Gly Glu Lys Cys Ile
    370                 375                 380

Val Arg Ser Phe Gly Ser Thr Thr Met Ala Lys Ala Phe Thr Val Thr
385                 390                 395                 400

Gln Met Ala Glu Cys Arg Thr Met Arg Leu Phe Asp His Glu Asn Val
                405                 410                 415

Asn Arg Phe Leu Gly Leu Ser Leu Asp Gly Ala Asn Val Leu Ala Val
            420                 425                 430

Trp Asn Phe Cys Met Arg Gly Ser Ile Arg Asp Val Ile Leu Ser Glu
        435                 440                 445

Asn Ala Met Val Lys Asp Val Ile Phe Ile Gln Ser Ala Ile Lys Glu
    450                 455                 460

Ile Cys Glu Gly Ile His Phe Leu His Asn Ser Pro Leu Gln Phe His
465                 470                 475                 480

Gly Arg Leu Lys Ser Ser Ala Cys Leu Ile Asn Asp Arg Trp Gln Val
                485                 490                 495

Lys Ile Ser Tyr Phe Gly Leu Arg Trp Leu Lys Ser Ser Gln Lys Asn
            500                 505                 510

Arg Ala Lys Asp Leu Leu Trp Leu Ser Pro Glu Gln Leu Arg Lys Met
        515                 520                 525

Gly Asp Ser Glu Ile Val Glu Gly Ser Lys His Ser Asp Ile Tyr Thr
    530                 535                 540

Met Ala Leu Ile Phe Thr Glu Met Val Asn Met Ser Pro Cys Trp Asp
545                 550                 555                 560

Ser Ser Glu Ala Asp Gly Ala Glu Ala Asp Arg Ala Glu Asp Gly Glu
                565                 570                 575

Glu Gln Asn Gly Thr Glu Met Ser Arg Arg Lys Gln Thr Ala Glu Thr
            580                 585                 590

Glu Gly Glu Thr Ala Gln Arg Arg Pro Gly Arg Arg Ala Arg Gly Arg
        595                 600                 605

Asn Ala Glu Glu Ile Ala Tyr Leu Val Lys Arg Gly Gly Ile Val Pro
    610                 615                 620

Leu Arg Pro Ile Ile Arg Pro Ala Phe Asp His Leu Asn Thr Glu Val
625                 630                 635                 640

Ile His Leu Ile Arg Asp Cys Trp Val Glu Thr Pro Ser Glu Arg Pro
                645                 650                 655

Thr Ile Glu Lys Val Arg Gln Lys Leu Arg Gln Met Gly Ala Gln Arg
            660                 665                 670

Arg Val Asn Leu Met Asp His Val Phe Asp Met Leu Glu Gln Tyr Ala
        675                 680                 685
```

-continued

```
Asn Lys Leu Glu Glu Glu Val Gln Glu Arg Thr Lys Glu Leu Glu Gly
    690                 695                 700

Glu Lys Arg Lys Ser Asp Ile Leu Leu Tyr Arg Met Met Pro Arg Gln
705                 710                 715                 720

Val Ala Asp Arg Leu Lys Leu Gly Gln Ser Val Glu Pro Glu Gln Phe
                725                 730                 735

Asp Cys Val Thr Val Phe Phe Ser Asp Ile Val Gln Phe Ala Ala Leu
            740                 745                 750

Ser Asn Gln Met Arg Pro Leu Gln Val Val Asn Leu Met Asn Glu Leu
        755                 760                 765

Tyr Thr Ile Phe Asp Ala Ile Ile Asp Glu His Asp Val Tyr Lys Gly
    770                 775                 780

Asp Gly Tyr Leu Cys Val Ser Gly Leu Pro Asn Arg Asn Gly Thr Leu
785                 790                 795                 800

His Ala Lys His Cys Ala Asp Met Ala Ile Lys Phe Met Gln Ala Leu
                805                 810                 815

Leu Asn Phe Arg Ile Pro Asp Leu Pro Asn Glu Arg Val Arg Leu Arg
            820                 825                 830

Ile Gly Leu His Ser Gly Pro Cys Val Ala Gly Val Val Gly Leu Ala
        835                 840                 845

Met Pro Arg Tyr Cys Leu Phe Gly Asp Thr Val Asn Thr Ala Ser Arg
    850                 855                 860

Met Glu Ser Ser Ser Ser Pro Asn Lys Ile His Met Ser Ser Glu Thr
865                 870                 875                 880

Leu Glu Leu Leu His Lys Asn Phe Asn Gly Ser Tyr His Thr Glu Ser
                885                 890                 895

Arg Gly Glu Val Ile Ile Lys Gly Lys Gly Val Met Glu Thr Phe Trp
            900                 905                 910

Leu Leu Gly Gln Val Glu Asn Gly Thr Thr Ile Asn Ala Asp Tyr Ala
        915                 920                 925

His Arg Met His Leu Pro Val Ile Lys Phe Gly Glu Glu Gly Asn Glu
    930                 935                 940

Thr Gly Lys Asn Ala
945


<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 8

agcggatccc gtccgcgcat ggacattgtg                                        30


<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 9

ccgctcgagc gttgcggcac tcgcatttct                                        30
```

The foregoing is illustrative of the present invention, and is not to be construed as limiting thereof. The invention is defined by the following claims, with equivalents of the claims to be included therein.

That which is claimed is:

1. An isolated DNA encoding a nematode guanylyl cyclase chemoreceptor selected from the group consisting of:

(a) isolated DNA having a nucleotide sequence selected from the group consisting of SEQ ID NO: 1 and SEQ ID NO: 3; and (b) isolated DNA that differs from the DNA of (a) above due to the degeneracy of the genetic code, and encodes a nematode guanylyl cyclase chemoreceptor encoded by (a) above.

2. An isolated DNA according to claim 1, which nematode guanylyl cyclase chemoreceptor is selected from the group consisting of order Tylenchida and order Aphelenchida chemoreceptors.

3. An isolated DNA according to claim 1, which nematode guanylyl cyclase chemoreceptor is selected from the group consisting of cyst nematode, root knot nematode, lesion nematode, and reniform nematode chemoreceptors.

4. An isolated DNA according to claim 1 having a nucleotide sequence according to SEQ ID NO: 1.

5. An isolated DNA according to claim 1, having a nucleotide sequence according to SEQ ID NO: 3.

6. An oligonucleotide that consists of about 15 to about 60 nucleotides of an isolated DNA of claim 1, or the complement of said oligonucleotide.

7. An oligonucleotide according to claim 6, wherein said oligonucleotide is DNA or RNA.

8. An expression cassette comprising a DNA according to claim 1 and a heterologous promoter operatively associated therewith.

9. A cell that contains an expression cassette of claim 8 and expresses said nematode guanylyl cyclase chemoreceptor.

10. A cell according to claim 9, which cell is a yeast cell.

11. A cell according to claim 9, which cell is a plant cell.

12. A cell according to claim 9, which cell is an insect cell.

* * * * *

UNITED STATES PATENT AND TRADEMARK OFFICE
CERTIFICATE OF CORRECTION

PATENT NO. : 6,521,438 B1
DATED : February 18, 2003
INVENTOR(S) : Davis et al.

It is certified that error appears in the above-identified patent and that said Letters Patent is hereby corrected as shown below:

Title page,
Item [56], References Cited, PUBLICATIONS, Yu reference should read as follows:

-- Yu et al.; Guanylyl Cyclase Expression in Specific Sensory Neurons: A New Family of Chemosensory Receptors, *Proc. Natl. Acad. Sci. USA*, 94:3384-3387 (1997).

The following references should be included under References Cited:
PUBLICATIONS:

-- Bargmann, Cornelia I., *Neurobiology of the Caenorhabditis elegans Genome*, Science, Vol. 282, pp. 2028-2033 (22 December 1998)

Wedel, Barbara J., et al., *New insights on the functions of the guanylyl cyclase receptors*, Federation of European Biochemical Societies Letters, Vol. 410, pp. 29-33 (1997)

Yu , Sidney, *Guanylyl cyclase expression in specific sensory neurons: A new family of chemosensory receptors*, Proc. Natl. Acad. Sci. USA, Vol. 94, pp. 3384-3387 (April 1997)

Abstract, Yan, Y, et al., *A putative chemosensory receptor gene in the soybean cyst nematode*, Phytopathology, Vol. 89, No. 6 Suppl., pg. S87 (June 1999)

Sequence Data, Yan, Y., et al., *Guanylyl cyclase from soybean cyst nematode*, Database EMBL 'Online!, XP-002166976 (11 November 1998)

UNITED STATES PATENT AND TRADEMARK OFFICE
CERTIFICATE OF CORRECTION

PATENT NO. : 6,521,438 B1
DATED : February 18, 2003
INVENTOR(S) : Davis et al.

It is certified that error appears in the above-identified patent and that said Letters Patent is hereby corrected as shown below:

PUBLICATIONS cont'd,

Sequence Data, Yan, Y., et al., *Heterodera glycines beta-1,4-endoglucanase precursor (HG-eng-1) gene, complete cds*, Database EMBL 'Online!, XP-002166977 (5 May 1998)

International Search Report, International Application No. PCT/US00/30295 dated May 23, 2001 --

Signed and Sealed this

Thirtieth Day of September, 2003

JAMES E. ROGAN
*Director of the United States Patent and Trademark Office*